US011376231B2

(12) United States Patent
Black et al.

(10) Patent No.: US 11,376,231 B2
(45) Date of Patent: Jul. 5, 2022

(54) COMPOSITIONS OF BIOACTIVE FULVATE FRACTIONS AND USES THEREOF

(71) Applicant: OMNI BIOCEUTICAL INNOVATIONS, INC., Phoenix, AZ (US)

(72) Inventors: Gary W. Black, Pottstown, PA (US); Jane Christensen, Phoenix, AZ (US); Farhan Taghizadeh, Phoenix, AZ (US)

(73) Assignee: OMNI BIOCEUTICAL INNOVATIONS, INC., Scottsdale, AZ (US)

( * ) Notice: Subject to any disclaimer, the term of this patent is extended or adjusted under 35 U.S.C. 154(b) by 0 days.

(21) Appl. No.: 16/805,606

(22) Filed: Feb. 28, 2020

(65) Prior Publication Data

US 2020/0368189 A1 Nov. 26, 2020

Related U.S. Application Data

(60) Continuation of application No. 15/812,855, filed on Nov. 14, 2017, now abandoned, which is a division of application No. 15/360,279, filed on Nov. 23, 2016, now Pat. No. 9,820,953.

(60) Provisional application No. 62/300,541, filed on Feb. 26, 2016.

(51) Int. Cl.
*A61K 31/194* (2006.01)
*A61K 8/96* (2006.01)
*A61Q 19/00* (2006.01)
*A61K 31/352* (2006.01)
*A61Q 19/08* (2006.01)
*A61K 35/10* (2015.01)
*A61K 8/36* (2006.01)
*A61K 8/64* (2006.01)
*A61K 9/00* (2006.01)
*A61K 45/06* (2006.01)

(52) U.S. Cl.
CPC .............. *A61K 31/194* (2013.01); *A61K 8/36* (2013.01); *A61K 8/64* (2013.01); *A61K 8/965* (2013.01); *A61K 9/0014* (2013.01); *A61K 31/352* (2013.01); *A61K 35/10* (2013.01); *A61K 45/06* (2013.01); *A61Q 19/00* (2013.01); *A61Q 19/08* (2013.01); *A61K 2800/91* (2013.01); *A61K 2800/92* (2013.01)

(58) Field of Classification Search
None
See application file for complete search history.

(56) References Cited

U.S. PATENT DOCUMENTS

| 8,518,879 | B2 | 8/2013 | Al-Qahtani |
| 9,119,974 | B2 | 9/2015 | Al-Qahtani |
| 2007/0212434 | A1 | 9/2007 | Day et al. |
| 2007/0224150 | A1* | 9/2007 | Chung ............... A61K 38/1808 424/70.14 |
| 2014/0175330 | A1 | 6/2014 | Black |
| 2015/0216839 | A1 | 8/2015 | Black |

FOREIGN PATENT DOCUMENTS

| CN | 105259011 | | 1/2016 | |
| EP | 2229960 | A1 | 9/2010 | |
| JP | H05-506673 | | 9/1993 | |
| JP | 2014-139201 | | 6/2009 | |
| JP | 2014-508160 | | 9/2012 | |
| WO | WO 1992/14480 | | 9/1992 | |
| WO | WO 00/19999 | | 4/2000 | |
| WO | WO 2011/139246 | | 11/2011 | |
| WO | WO 2012/121695 | | 9/2012 | |
| WO | WO 2014/047292 | * | 3/2014 | ............... A61K 8/60 |

OTHER PUBLICATIONS

Sai et al., "Tigerinins: Novel Antimicrobial Peptides from the Indian Frog*Rana tigerina*", The Journal of Biological Chemistry, Oct. 12, 2000, vol. 276, No. 4 (2001), pp. 2701-2707.
Office Action issued in Japanese application No. 2018-564721, dated Jan. 18, 2021.
PCT Search Report and Written Opinion in PCT Application No. PCT/US2016/064454, filed Dec. 1, 2016, dated Mar. 10, 2017.
Sabi, et al., "Carbohydrate-derived Fulvic acid (CHD-FA) inhibits Carrageenan-induced inflammation and enhances wound healing: efficacy and Toxicity study in rats", Drug Development Research, vol. 73, No. 1, p. 18-23 (Feb. 2012).
Tang, et al., "A Small Peptide with Potential Ability to Promote Wound Healing", PLOS ONE, vol. 9, No. 3, E92082, p. 1-10 (Mar. 2014).
Anonymous: "SE208 (Synepin)", Feb. 1, 2012 (Feb. 1, 2012 ), Retrieved from the Internet: URL:http://www.equipforskin.com/synepin.html [retrieved on Feb. 20, 2017].
Anonymous: "SE204 (Syndermin)", Feb. 1, 2012 (Feb. 1, 2012 ), Retrieved from the Internet: URL:http://www.equipforskin.com/syndermin.html [retrieved on Feb. 20, 2017].
Anonymous: "SE214 (Adiponin)", Jan. 1, 2012 (Jan. 1, 2012 ), Retrieved from the Internet: URL:http://www.equipforskin.com/adiponin_.html [retrieved on Feb. 20, 2017].
Anonymous : "SE209 (Binterin)", Jan. 1, 2012 (Jan. 1, 2012 ), Retrieved from the Internet: URL:http://www.equipforskin.com/binterin.html [retrieved on Feb. 20, 2017].

(Continued)

*Primary Examiner* — Craig D Ricci
(74) *Attorney, Agent, or Firm* — Knobbe, Martens, Olson & Bear LLP

(57) ABSTRACT

Compositions with fulvate fractions alone or in combination with growth factors, bioactive fragmented peptides, or combinations thereof are disclosed herein. Also disclosed are methods of using said compositions for the catalyzing cellular regeneration, including the healing, treatment, or prevention of skin disorders. Also disclosed are methods for extracting, isolating, and purifying fulvate fractions for use in the manufacture of said compositions.

11 Claims, 9 Drawing Sheets

Specification includes a Sequence Listing.

(56) References Cited

OTHER PUBLICATIONS

Anonymous: "SE215 (Winhibin)", Jan. 1, 2012 (Jan. 1, 2012), Retrieved from the Internet: URL:http://www.equipforskin.com/winhibin.html [retrieved on Feb. 20, 2017].

Buffle J., Greter F. L., Haerdi W., 1977, Measurements of Complexation Properties of Humic and Fulvic Acids in Natural Water, With Lead & Copper Ion-Selective Electrodes. Anal. Chem. 49: 216-222.

Drozd J., 1978, Studies of chemical and physiochemical properties of humus compounds of some taxonomic soil units, Rosprawy Naukowe, Zeszyt 13, AR Wroclaw pp. 65.

Flerus et al (Biogeosciences 9: 1935-1955, 2012) (Year: 2012).

Hiradate et al (Soil Sci and Plant Nutrition 53:413-419, 2007) (Year: 2007).

Mccalley et al (J Chromatogr A 1217:858-880, 2010) (Year: 2010).

Van Rensburg: "The Antiinflammatory Properties of Humic Substances: A Mini Review", Phytotherapy Research., vol. 29, No. 6, Mar. 3, 2015 (Mar. 3, 2015), pp. 791-795.

Wu et al (Applied Geochemistry 22: 1598-1605, 2007) (Year: 2007).

Balabanova-Radonova et al., "Use of HPLC in fractionation of lignite humic substances", FUEL 1980, vol. 59, Iss. 4, Apr.

Office Action issued in JP application No. 2020-219082, dated Feb. 18, 2022.

\* cited by examiner

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: SLPI Primer 1

<400> SEQUENCE: 1
atgaagtcca gcggcctc                                                 18

<210> SEQ ID NO 2
<211> LENGTH: 23
<212> TYPE: DNA
<213> ORGANISM: Artificial Sequence
<220> FEATURE:
<223> OTHER INFORMATION: SLPI Primer 2

<400> SEQUENCE: 2
aagagaaata ggctcgttta ttt                                           23

<210> SEQ ID NO 3
<211> LENGTH: 19
```

```
<212> TYPE: DNA
<213> ORGANISM: Artificial Sequence
<220> FEATURE:
<223> OTHER INFORMATION: hBD-1 Primer 1

<400> SEQUENCE: 3
gctcagcctc caaaggagc                                              19

<210> SEQ ID NO 4
<211> LENGTH: 25
<212> TYPE: DNA
<213> ORGANISM: Artificial Sequence
<220> FEATURE:
<223> OTHER INFORMATION: hBD-1 Primer 2

<400> SEQUENCE: 4
aaaagaatgc ttataaaaag ttcat                                       25

<210> SEQ ID NO 5
<211> LENGTH: 23
<212> TYPE: DNA
<213> ORGANISM: Artificial Sequence
<220> FEATURE:
<223> OTHER INFORMATION: hBD-3 Primer 1

<400> SEQUENCE: 5
ggaatcataa acacattaca gaa                                         23

<210> SEQ ID NO 6
<211> LENGTH: 25
<212> TYPE: DNA
<213> ORGANISM: Artificial Sequence
<220> FEATURE:
<223> OTHER INFORMATION: hBD-3 Primer 2

<400> SEQUENCE: 6
cgggaatcat aaacacatta cagaa                                       25

<210> SEQ ID NO 7
<211> LENGTH: 19
<212> TYPE: DNA
<213> ORGANISM: Artificial Sequence
<220> FEATURE:
<223> OTHER INFORMATION: hBD-4 Primer 1

<400> SEQUENCE: 7
gcagccccag cattatgca                                              19

<210> SEQ ID NO 8
<211> LENGTH: 21
<212> TYPE: DNA
<213> ORGANISM: Artificial Sequence
<220> FEATURE:
<223> OTHER INFORMATION: hBD-4 Primer 2

<400> SEQUENCE: 8
aagctactga ggtcctactt c                                           21

<210> SEQ ID NO 9
<211> LENGTH: 12
<212> TYPE: PRT
<213> ORGANISM: Fejervarya cancrivora

<400> SEQUENCE: 9

Arg Val Cys Ser Ala Ile Pro Leu Pro Ile Cys His
 1               5                  10
```

```
<210> SEQ ID NO 10
<211> LENGTH: 12
<212> TYPE: PRT
<213> ORGANISM: Fejervarya cancrivora

<400> SEQUENCE: 10

Arg Val Cys Met Ala Ile Pro Leu Pro Leu Cys His
                5                   10

<210> SEQ ID NO 11
<211> LENGTH: 11
<212> TYPE: PRT
<213> ORGANISM: Fejervarya cancrivora

<400> SEQUENCE: 11

Trp Cys Lys Pro Lys Pro Lys Pro Arg Cys His
                5                   10
```

COMPOSITIONS OF BIOACTIVE FULVATE FRACTIONS AND USES THEREOF

CROSS-REFERENCE TO RELATED APPLICATIONS

The present application is a continuation application of U.S. patent application Ser. No. 15/812,855, filed Nov. 14, 2017, which is a divisional application of U.S. patent application Ser. No. 15/360,279, filed Nov. 23, 2016, which issued as U.S. Pat. No. 9,820,953 on Nov. 21, 2017, and which claims the benefit of priority to U.S. Provisional Patent Application No. 62/300,541, filed Feb. 26, 2016, each disclosure of which is incorporated by reference herein in its entirety.

REFERENCE TO SEQUENCE LISTING

The present application is being filed along with a Sequence Listing in electronic format. The Sequence Listing is provided as file SeqListingOBINN-001C1.txt created and last modified on Feb. 28, 2020, which is 2,286 bytes in size. The information in the electronic format of the Sequence Listing is incorporated herein by reference in its entirety.

FIELD OF THE DISCLOSURE

The present disclosure relates generally to the field of cellular regeneration, including the healing of wounds and treatments and improvements of skin conditions. In particular, the disclosure relates to compositions having isolated bioactive fulvate fractions for use in cellular regeneration.

BACKGROUND

Humic substances (HS) are ubiquitous in nature and arise from the decay of plant and animal residue in the environment. HS are among the most widely distributed natural products on the surface of the earth, and are the major organic components of soil (humus), lakes, rivers and geological deposits such as peat, leonardite, lignite (brown coal), and organic clays. Humified organic matter (HOM) is relatively stable, but can vary in composition based on its location, deposit type, depth, and age. HOM contains a complex mixture of organic molecules, such as bioactive polyelectrolytes (BPs).

BPs include numerous bioactive, naturally occurring, related, but not identical, high molecular-weight polymers. Examples of BPs include, but are not limited to, fractions of HS, such as humic acid (HA), fulvic acid (FA), humin, or uletic acid (UA). The differences among BPs include a considerable variation in molecular weight and size, the number of functional groups (e.g., carboxyl, phenolic HO), and the extent of polymerization that has taken place. HA and FA have received broad international attention within the scientific community due to their wide range of bioactive characteristics. See, e.g., Drozd 1978, Studies of chemical and physiochemical properties of humus compounds of some taxonomic soil units, *Rosprawy Naukowe, Zeszyt* 13, *AR Wroclaw* pp. 65. BPs are useful for multiple functions in humans, other animals, and plants.

Despite extensive research directed to understanding the formation and composition of HOM, the precise chemical structure of the constituents of HOM remains unknown. HOMs that have been isolated from different sources experienced different environments, oxidative states, and humification processes; thus they typically exhibit widely varying compositions. These variations result in the production of a vast and complex array of BPs that range in molecular weights from 60 to 300,000 Da and whose polymers vary in length from a few nanometers to several microns.

Certain HS, such as peat-derived bioactive products, have been used for treating skin and other conditions. The skin is the largest organ and its primary function is to serve as a protective barrier against outside environment and excessive water loss. Skin consists of two main tissue layers: a keratinized stratified epidermis and an underlying thick layer of collagen-rich dermal connective tissue providing support and nourishment. Impaired wound healing is a major complication underlying several disease processes (such as diabetes). Efficient wound healing is hampered by a wide variety of processes including hypoxia (oxygen deprivation), inflammation, infection, and oxidative stress through the generation of harmful reactive oxygen species (ROS). The inherent complexity of wound healing has resulted in limited efficacy of most therapies that target single parameters involved in the slow healing processes.

SUMMARY

The present disclosure is directed to compositions including an isolated fulvate fraction alone or in combination with one or more growth factor or bioactive peptide, for use in cell regeneration, including for the treatment of tissue repair and wound healing. Also provided herein are methods for extracting, refining, and formulating said compositions.

In some embodiments is provided a composition including an isolated fulvate fraction. In some embodiments, the fulvate fraction has an average molecular weight ranging from 80 to 1200 Da, as measured by vapor pressure osmometry. In some embodiments, the fulvate fraction has an average molecular weight ranging from 80 to 350 Da, as measured by vapor pressure osmometry. In some embodiments, the fulvate fraction has an average molecular weight ranging from 300 to 320 Da, as measured by vapor pressure osmometry. In some embodiments, the fulvate fraction has a number average molecular weight of about 309 Da, as measured by vapor pressure osmometry. In some embodiments, the average molecular weight is 308.24 Da, as measured by vapor pressure osmometry. In some embodiments, the isolated fulvate fraction is referred to herein as M-007. In some embodiments, M-007 is isolated from humified organic matter (HOM). In some embodiments, M-007 has an approximate formula of $C_{12}H_{16}O_9$. In some embodiments, the composition is a topical composition. In some embodiments, the topical composition can be formulated as a liquid, a lotion, a cream, a foam, a gel, a powder, or an ointment. In some embodiments, the composition is a transdermal composition formulated as a patch. In some embodiments, the composition is a nasal composition formulated as a drop, a spray, or an ointment. In some embodiments, the composition is a sublingual composition. In some embodiments, the composition is an injectable composition.

In some embodiments, the composition further includes, for example, one or more growth factor, one or more bioactive fragmented peptide, or combinations thereof. In some embodiments, the one or more growth factor is an amino acid, a nucleic acid, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), an insulin-like growth factors (IGF-I and IGF-II), an interleukin cytokine (IL-1α, IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), or a combination thereof.

In some embodiments, the composition further includes one or more bioactive fragmented peptide. As used herein, a bioactive peptide is a compound consisting of two or more amino acids linked in a chain, the carboxyl group of each acid being joined to the amino group of the next by a bond of the type =OC=NH. In some embodiments, the one or more bioactive fragmented peptide is an antihypertensive peptide, an antioxidative peptide, an antithrombotic peptide, a hypocholesterolemic peptide, an opioid peptide, a mineral-binding peptide, an anti-appetizing peptide, an antimicrobial peptide, an immunomodulatory peptide, a cytomodulatory peptide, or fragments, and/or combinations thereof. In some embodiments, the one or more bioactive peptide is a collagenase-derived biologically active fragment, a tigerinin-based peptide, or combinations thereof. In some embodiments, the bioactive fragmented peptide is a salamander skin peptide, such as a tylotoin-based peptide. In some embodiments, the fragmented peptide is a frog skin peptide, such as a tigeiinin-based peptide. In some embodiments, the fragmented peptide is Syndermin palmitoyl tripeptide-1 amide, Synepin palmitoyl sh-tripeptide-3 amide, Binterin palmitoyl sh-tripeptide-4 amide, Winhibin palmitoyl sh-tripeptide-53 amide, Adiponin palmitoyl sh-tripeptide-1 amide, or combinations thereof.

In some embodiments, the composition alone or further including one or more growth factor, one or more bioactive fragmented peptide, or combinations thereof is used for the treatment of a subject in need of cell regeneration. In some embodiments, the subject in need of cell regeneration suffers from a chronic, accidental, or surgical wound. In some embodiments, the subject in need of cell regeneration suffers from a skin condition.

In some embodiments is provided a method for relieving, treating, improving, ameliorating, or causing regression of a wound of skin condition in a subject in need thereof. In some embodiments, the method includes selecting a subject in need thereof. In some embodiments, the subject suffers from one or more surgical, accidental, or chronic wound or skin condition. In some embodiments, the method includes topically applying a therapeutically effective amount of a topical composition including a fulvate fraction. In some embodiments, the fulvate fraction is M-007.

In some embodiments, the method includes relieving, treating, improving, ameliorating, or causing regression of a skin condition. In some embodiments, the skin condition is rhytide, non-enzymatic glycosylation of the skin, sun damage, smoking damage, fibrosis of the skin, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidalis nuchae, nuchal keloid acne), adult forehead with scattered red pimples, acne vulgaris, dyshidrosis, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuir s disease), idiopathic facial aseptic granuloma, infantile acne, lupoid rosacea (granulomatous rosacea, micropapular tuberculid, rosacea-like tuberculid of Lewandowsky), lupus miliaris disseminates faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer (carcinoma and melanoma), tropical acne, psoriasis, including plaque psoriasis, guttate psoriasis, inverse psoriasis, pustular psoriasis, erythrodermic psoriasis, nail psoriasis, psoriatic arthritis, or combinations thereof.

In some embodiments is provided a method for extracting a bioactive polyelectrolyte from humified organic matter (HOM). In some embodiments, the bioactive polyelectrolyte includes a fulvate fraction. In some embodiments, the fulvate fraction is M-007. In some embodiments, the method for extraction includes providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method includes isolating a fulvate fraction. In some embodiments, the fulvate fraction is M-007.

Some embodiments provided herein related to a transdermal drug delivery system including an isolated fulvate fraction. In some embodiments, the transdermal drug delivery system includes an isolated fulvate fraction in an amount of about 0.5% to about 65% by weight. In some embodiments, the isolated fulvate fraction is present in an amount of about 0.5% to about 7% by weight. In some embodiments, the isolated fulvate fraction is M-007. In some embodiments, the transdermal drug delivery system provides an amount of isolated fulvate fraction in an amount of about 10-50 times greater than other modes of administration. In some embodiments, the transdermal drug delivery system enhances the delivery of the isolated fulvate fraction from about 150% to about 350%, as compared to non-enhanced formulations.

These features, together with other features herein further explained, will become obvious through a reading of the following description of the drawings and detailed description.

BRIEF DESCRIPTION OF THE DRAWINGS

The description herein is understood from the following detailed description when read in conjunction with the accompanying drawings. It is emphasized that, according to common practice, the various features of the drawings are not to-scale. On the contrary, the dimensions of the various features are arbitrarily expanded or reduced for clarity, Included in the drawings are the following figures.

DETAILED DESCRIPTION

Figure 1:
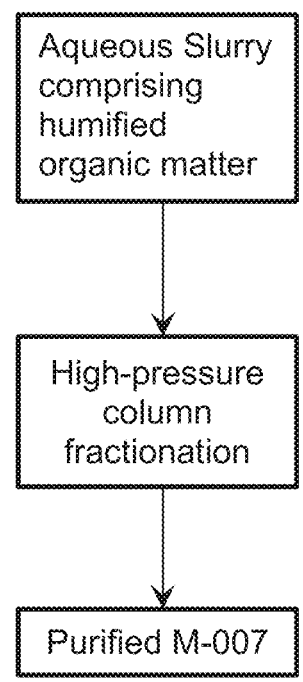
FIG. 1 is a schematic representation of the purification method of M-007.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

As summarized above, aspects of the compositions of fulvate fractions and methods of treatment with the fulvate fractions are provided herein. The methods also include methods for extracting, refining, and formulating said compositions.

It is to be understood that this disclosure is not limited to particular embodiments described, as such may, of course, vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Definitions

Unless defined otherwise, technical and scientific terms used herein have the same meaning as commonly understood by one of ordinary skill in the art to which the present disclosure belongs. For purposes of the present disclosure, the following terms are defined below.

As used herein, the term "treatment" refers to an intervention made in response to a disease, disorder or physiological condition manifested by a subject, particularly a subject suffering from one or more wound or skin disorder. The aim of treatment may include, but is not limited to, one or more of the alleviation or prevention of symptoms, slowing or stopping the progression or worsening of a wound, disease, disorder, or condition and the remission of the wound, disease, disorder, or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments, treatments reduce, alleviate, or eradicate the symptom(s) of the disease(s).

As used herein, the term "prevention" refers to any activity that reduces the burden of the individual later expressing disease symptoms. This can take place at primary, secondary, and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as topical, oral, or intravenous application, and administered in the form of a conventional pharmaceutical preparation, such as solid such as tablets, granules, powders, capsules, and liquid such as solution, emulsion, suspension, creams, lotions, ointments, gels, and the like. Often the physiologically acceptable carrier is an aqueous pH buffered solution such as phosphate buffer or citrate buffer. The physiologically acceptable carrier may also include, for example, one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counter ions such as sodium, and nonionic surfactants such as Tween™, polyethylene glycol (PEG), and Pluronics™. Auxiliary, stabilizer, emulsifier, lubricant, binder, pH adjustor controller, isotonic agent, and other conventional additives may also be added to the carriers.

The pharmaceutically acceptable or appropriate carrier may include other compounds known to be beneficial to an impaired situation of the skin, (e.g., antioxidants, such as Vitamin C, Vitamin E, Selenium or Zinc); or a food composition. The food composition can be, but is not limited to, milk, yogurt, curd, cheese, fermented milks, milk based fermented products, ice-creams, fermented cereal based products, milk based powders, infant formulae, tablets, liquid bacterial suspensions, dried oral supplement, or wet oral supplement.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In certain embodiments, the "purity" of any given agent (e.g., fulvate fraction, growth factor, etc.) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

As used herein, the terms "function" and "functional" and the like refer to a biological, enzymatic, or therapeutic function.

The term "isolated" is meant material that is substantially or essentially free from components that normally accompany it in its native state. For example, an "isolated bioactive fulvate fractions," as used herein, includes a fulvate fraction that has been purified from its naturally-occurring state, e.g., a fulvate fraction which has been removed from the humified organic matter in which it naturally resides.

As used herein, the term "bioactive" refers to substances having a biological effect on a living organism. A substance that is bioactive may have properties including anti-inflammatory, anti-microbial, anti-irritant, and anti-oxidant effects as well as the acceleration and improvement of wound healing.

The term "half maximal effective concentration" or "$EC_{50}$" refers to the concentration of an antibody or other agent described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to activity related to symptoms or pathology of skin disorders. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of an antibody or other agent is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 1 8, 19, 20, 25, 30, 40, 50, 60, 70, 80, 90, or 100 nM, Preferably, biotherapeutic compositions will have an $EC_{50}$ value of about 1 nM or less.

The term "modulating" includes "increasing" or "stimulating," as well as "decreasing" or "reducing," typically in a statistically significant or a physiologically significant amount as compared to a control. An "increased" or "enhanced" amount is typically a "statistically significant" amount, and may include an increase that is 1.1, 1.2, 2, 3, 4, 5, 6, 7, 8, 9, 10, 1 5, 20, 30, or more times (e.g., 500, 1000 times) (including all integers and decimal points in between and above 1, e.g., 1.5, 1.6, 1.7, 1.8, etc.) the amount produced by no composition (the absence of an agent or compound) or a control composition. A "decreased" or reduced amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 75%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. As one non-limiting example, a control in comparing canonical and non-canonical activities could include the activity antagonist activity) or of a formulation composition, such as, for example, a fulvate fraction, towards a skin disorder relative to no treatment, a placebo treatment, or a control treatment. Other examples of "statistically significant" amounts are described herein.

The term "solubility" refers to the property of a fulvate fraction, peptide, or other agent provided herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH. In certain embodiments, solubility is measured in water or a physiological buffer such as PBS. In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/mL at room temperature or at 37° C.

A "subject," as used herein, includes any animal that exhibits a symptom, or is at risk for exhibiting a symptom, of one or more disorder such as rhytide, non-enzymatic glycosylation of the skin, sun damage, smoking damage, fibrosis of the skin, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidalis nuchae, nuchal keloid acne), adult forehead with scattered red pimples, acne vulgaris, dyshidrosis, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes fines, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminates faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer (carcinoma and melanoma), tropical acne, psoriasis, including plaque psoriasis, guttate psoriasis, inverse psoriasis, pustular psoriasis, erythrodermic psoriasis, nail psoriasis, psoriatic arthritis, or combinations thereof, among others described herein and known in the art. Also included are subjects for whom it is desirable to profile presence and/or levels of disorder-associated markers, for diagnostic or other purposes. In certain aspects, a subject includes any animal having a wound or skin disorder, as described herein and known in the art. Suitable subjects (patients) include laboratory animals (such as mouse, rat, rabbit, or guinea pig), farm animals, and domestic animals or pets (such as a cat or dog). Non-human primates and, preferably, human patients, are included.

Disorders

As provided herein, a method of treating a subject in need is provided. The subject in need can have diseases, disorders, ailments, and/or damage of skin, hair, and/or nails. In some embodiments, the subject can have an oral disease of the mouth. In some embodiments, the subject suffers from an ocular disease of the ear. In some embodiments, the subject suffers from inflammation. In some embodiments, the subject can have a wound.

Besides providing a structural barrier, the skin contains several immune cells that can be activated by invading pathogens or skin damage. One of the most important immune cells involved in wound healing is the macrophage, which exhibits different immunological functions in the skin, including phagocytosis and antigen-presentation. Furthermore, they can produce many cytokines and chemokines to orchestrate the wound healing process throughout the different phases.

"Skin damage" as described herein, can refer to damage to the skin that can be caused by aging, sun damage, cancer, skin disorder or skin diseases that can cause irritation of the skin. Without being limiting, the "skin diseases" and/or "skin disorders" can include rhytide, non-enzymatic glycosylation of the skin, sun damage, smoking damage, fibrosis of the skin, acne aestivalis (Mallorca acne), acne conglobate, acne cosmetica (cosmetic acne), acne fulminans (acute febrile ulcerative acne acne keloidalis nuchae (acne keloidalis, dermatitis papillaris capillitii, folliculitis keloidalis, folliculitis keloidalis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes flies, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminates faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne, psoriasis, including plaque psoriasis, guttate psoriasis, inverse psoriasis, pustular psoriasis, erythrodermic psoriasis, nail psoriasis, psoriatic arthritis, and combinations and/or variations thereof. In some embodiments described herein, a method of treating a subject in need is provided. The subject can have a disease affecting the skin as provided described herein.

"Hair and scalp disorders" are diseases that affect the hair and scalp and are also described herein. Diseases that affect hair and scalp can include but are not limited to alopecia, androgenic alopecia, hirsutism, hair shaft disorders, inflammation, acromegaly, eczema, psoriasis, impetigo, atopic dermatitis, darier disease, and folliculitis. Common causes for scalp disorders can include but are not limited to acromegaly, atopic dermatitis, darier disease, eczema, fragile X syndrome, impetigo, pachydermoperiostosis, psoriasis, and. Rosenthal-Kloepfer syndrome. In some embodiments described herein, a method of treating a subject in need is provided. The subject can have a disease affecting the skin and scalp. In some embodiments the subject suffers from alopecia, androgenic alopecia, hirsutism, hair shaft disorders, inflammation, acromegaly, eczema, psoriasis, impetigo, atopic dermatitis, darier disease, and/or folliculitis. In some embodiments, the subject suffers from acromegaly, atopic dermatitis, darier disease, eczema, fragile X syndrome, impetigo, pachydermoperiostosis, psoriasis, and/or Rosenthal-Kloepfer syndrome. In some embodiments, the treating includes administering a formulation to the subject in need. In some embodiments, the formulation is within a hair cream, a hair gel, a scalp lotion, a shampoo, conditioner, hair spray, or a hair mousse.

"Nail diseases" are disorders or diseases that affect the nail, nail bed, or cuticle region and are also described herein. Diseases that affect the nail and surrounding skin area such as the cuticle can lead to infection or inflammation that could require medical assistance. Diseases that infect the nail, nail bed, and/or cuticle can include but is not limited to onychia, onychocryptosis, onychodystophy, onychogryphosis, onycholysis, onychomadesis, onychomycosis, tinea unguium, onychophosis, onychoptosis, onychorrhexis, paronychia, Koilonychia, subungual hematoma, onychomatricoma, nail pemphigus, erythronychia, and melanonychia. In some embodiments described herein, a method of treating a subject in need is provided. The subject can have a disease affecting the nails, nail bed, and/or cuticles. In some embodiments, the subject suffers from onychia, onychocryptosis, onychodystophy, onychogryphosis, onycholysis, onychomadesis, onychomycosis, tinea unguium, onychophosis, onychoptosis, onychorrhexis, paronychia, Koilonychia, subungual hematoma, onychomatricoma, nail pemphigus, erythronychia, and/or melanonychia. In some embodiments, the treating includes administering a formulation to the subject in need. In some embodiments, the formulation is within a skin cream, a lotion, a cuticle cream, or a nail polish.

"Oral health" as described herein, refers to the health of the teeth and the surrounding tissues such as the gums. Poor oral health can arise from poor oral hygiene, tooth decay, gum disease, diabetes, pregnancy, cancer, HPV, oral cancer (squamous cell carcinoma, verrucous carcinoma, minor salivary gland carcinomas, lymphomas), benign oral cavity, and oropharyngeal tumors (eosinophilic granuloma, fibroma, granular cell tumor, keratoacanthoma, leiomyoma, osteochondroma, lipoma, schwannoma, neurofibroma, papilloma, condyloma acuminatum, verruciform xanthoma, pyogenic granuloma, rhabdomyoma, odontogenic tumors), leukoplakia and erythroplakia, and tongue cancer. Cancer in the mouth can occur on and around the tongue, the gums, the roof of the mouth, and in the insides of the cheeks and lips. In some embodiments, a treatment is provided for maintenance of oral health for a subject in need. In some embodiments, the subject has poor oral hygiene, tooth decay, gum disease, diabetes, cancer, HPV, oral cancer (squamous cell carcinoma, verrucous carcinoma, minor salivary gland carcinomas, lymphomas), benign oral cavity, and oropharyngeal tumors (eosinophilic granuloma, fibroma, granular cell tumor, keratoacanthoma, leiomyoma, osteochondroma, lipoma, schwannoma, neurofibroma, papilloma, condyloma acuminatum, verruciform xanthoma, pyogeni c granuloma, rhabdomyoma, odontogenic tumors), leukoplakia and erythroplakia, or tongue cancer. In some embodiments, the subject is pregnant. In some embodiments, the treatment includes administering to the subject in need. In some embodiments, the formulation is in the form of a gargle or a rinse. In some embodiments, the formulation is in a gel, and the gel is administered in a teeth tray. In some embodiments, the formulation is a toothpaste, a prophylactic paste, a tooth polish, a dental solution, an oral spray, an oral rinse, a mouth wash, dental floss, chewing gum, a lozenge, or a tablet.

"Inflammation" as described herein, refers to a biological response of a body tissue to harmful stimuli. The harmful stimuli can include but is not limited to pathogens, bacteria, viruses, fungi, damaged cells, and other irritants that are known to those skilled in the art. Inflammation can be a protective immune response that can involve, for example, immune cells, white blood cells, blood vessels, molecular mediators, and other small molecules. Signs of inflammation can include but is not limited to pain, heat, swelling, and/or loss of function. Inflammation can be acute or chronic. In some embodiments described herein, a formation is provided for the treatment of inflammation. In some embodiments, the subject suffers from inflammation. In some embodiments, the inflammation is on the skin, scalp, nasal passages, mouth, nail area such as the cuticles, eyes, vaginal area or the perineal area.

"Auditory health" can refer to the health of the ear, inner ear, outer ear and surrounding areas. Auditory care can be required when a subject has inflammation in the ear, the ear canal and the surrounding tissues. Common irritants such as bacteria, viruses, mucus, and other skin conditions can lead to the inflammation of the ear. External irritations can also occur that can cause inflammation of the ear. For example, when water gets trapped in the ear canal, bacteria can spread which can then cause inflammation and pain. Inner ear inflammation can also occur following a viral infection such as flu or upper respiratory infection. The virus can then cause swelling of the balance organs leading to dizziness with or without pain during inner ear inflammation.

In some embodiments, a method of treating a subject suffering from an auditory inflammation or ear infection is provided. In some embodiments, the method includes providing the isolated fulvate fraction of any of the embodiments described herein or the topical formulation of any of the embodiments described herein and applying the isolated fulvate fraction or topical formulation to the subject. In some embodiments, the isolated fulvate fraction or topical formulation is applied into the ear. The topical formulation can include the isolated fulvate fraction made by the methods of any of the embodiments described herein or the isolated fulvate fraction of any of the embodiments described herein. The isolated fulvate fraction can be extracted, purified, and isolated by a method of any of the described embodiments herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007. In some embodiments, the formulation is in the form of ear drops, ear wash, or ear ointment.

As used herein, the term "high pressure column fractionation" refers to the use of at least one column under high pressure to separate unreacted components, reaction by-products, and/or low molecular weight excipients, thereby fractionating the slurry into various fractions based on size and properties.

As used herein, the term "molecular sieving" refers to passage of a sample through a one or more porous material having pore diameters of less than 50, 40, 30, 20, 10, 9, 8, 7, 6, 5, 4, 3, 2, 1, or 0.1 nm. The samples may be passed through such molecular sieves in tandem in order to obtain fractions of various size and properties from the aqueous slurry. In some embodiments, high pressure column fractionation can be used alone or in combination with molecular sieving to obtain a desired fulvate fraction for use in the treatment of skin diseases, disorders, or wounds.

Isolated Fulvate Fraction

As used herein, the term "bioactive polyelectrolyte" or "BP" refers to any bioactive polymer whose repeating units bear an electrolyte group, as well as the salts and esters of the bioactive polymer. BPs can have a wide and valuable range of beneficial uses in humans, other animals, and plants. BPs can be made up of five (5) basic elements: carbon, hydrogen, nitrogen, oxygen, and sulfur, with carbon and oxygen being the main components. The principal organic groups of BPs include, for example, phenolic, carboxylic, OH, aliphatic CH, carbonyl, conjugated carboxyl, aromatic $CH_2$ or $CH_3$, ionic carboxyl, and possibly others. BPs can be classified and, to some extent, identified by their degree of polymerization, molecular weight, and atomic particle size, characteristics that appear to be dictated by the extent and type of humification processes that produced the BPs.

Examples of BP include, but are not limited to, humic acid (HA), fulvic acid (FA), humin, and ulmic acid (UA). In general, fulvic acid includes low-molecular weight polymeric compounds, whereas humic acid includes high molecular weight polymeric compounds. The humic and fulvic acid fractions of BP are a combination of colloids and nano-crystalline materials. The HA and FA fractions have been shown to have excellent bioactive capabilities for living matters.

The molecular sizes of BPs vary widely and can be, for example, 150-13,000 Da for FA. As used herein, the term "fulvic acid," "fulvate," or "FA" refers to a fraction of humic substances that is soluble in water under all pH conditions. It is also soluble in methyl ethyl ketone, methyl alcohol, and acids. It generally has a yellow (fulvus) to yellow-brown color. Fulvate includes a mixture or collection of different acids containing carboxyl and phenolate groups.

The proposed structure of fulvate contains both aromatic and aliphatic structures that are extensively substituted with oxygen-containing functional groups. A proposed fulvate structure has been previously described (see Buffle J., Greter F. L., Haerdi W., 1977, Measurements of Complexation Properties of Humic and Fulvic Acids in Natural Water, With Lead & Copper Ion-Selective Electrodes. Anal. Chem. 49: 216-222; see also US Patent Application No. 2015/0216839; each of which are incorporated herein by reference in their entireties). As used herein, the term "fulvate" encompasses the esters, salts or ion complexes of fulvic acid.

Provided herein is a method for extracting and isolating specified fulvate fractions. The method may include, for example, providing an aqueous slurry having humified organic matter (HOM); applying the aqueous slurry to high pressure column fractionation to obtain fractionated samples; applying the fractionated samples to molecular sieving; and isolating a fulvate fraction. HOM contains fulvates ranging from a broad range of molecular weights. Provided herein are methods for isolated specified fulvate fractions that are useful for wound healing and for treating skin disorders and disease as described herein. In some embodiments, the fulvate fraction has an average molecular weight ranging from 80 to 1200 Da, as measured by vapor pressure osmometry. In some embodiments, the fulvate fraction has an average molecular weight ranging from 80 to 350 Da, as measured by vapor pressure osmometry. In some embodiments, the fulvate fraction has an average molecular weight ranging from 300 to 320 Da, as measured by vapor pressure osmometry. In some embodiments, the fulvate fraction has an average molecular weight of about 308.24 Da, as measured by vapor pressure osmometry. In some embodiments, the fulvate fraction has an average molecular weight of about 309 Da, as measured by vapor pressure osmometry. As described herein, "vapor pressure osmometry" refers to a nonspectroscopical technique for measuring the number average molecular weight of a polymer.

Using the method described herein, the numerous range of isolated fulvate fractions are limited to about 27 fulvate fractions. However, the fulvate fraction having the molecular weight of about 309 Da, is therapeutically effective for treating wounds and disorders. In some embodiments, the therapeutically effective isolated fulvate fraction is referred to herein as M-007. In some embodiments, M-007 has a range of acceptable molecular weights ranging from about 80 to about 1200 Da. In some embodiments, M-007 has a range of acceptable molecular formulas that correspond to the molecular weight. In some embodiments, M-007 has a general formula of $C_{12}H_{16}O_9$.

As used herein, an "isolated BP fraction" is a fraction that is substantially free of the non-BP substances present in the source where the BP fraction is isolated. An isolated HP fraction can be an isolated fraction of humic substances, such as an isolated FA fraction that is substantially free of the non-FA substances present in the source where the FA is isolated, an isolated HA fraction that is substantially free of the non-HA substances present in the source where the HA is isolated, etc. An isolated BP fraction can also contain two or more isolated fractions of humic substances, such as two or more of UA, HA, FA, and humin fractions, that is substantially free of the other substances. A BP fraction is "substantially free of" the non-BP substances when there is less than about 30%, 20%, 15%, 10%, 5%, 4%, 3%, or 2% and preferably less than 1%, by dry weight, of the non-BP substances (also referred to herein as "contaminating substances").

Methods of Treating a Disorder

In some embodiments, a method of treating a subject suffering from a disorder is provided. In some embodiments, the method includes administering to the subject a therapeutically effective amount of a composition, wherein the composition includes an isolated fulvate fraction. In some embodiments, the isolated fulvate fraction is M-007. In some embodiments, the composition further includes a growth factor, a bioactive peptide fragment, or combinations thereof.

As used herein, "administration" or "administering" is defined as providing a pharmaceutical composition described herein to a mammal (e.g., a human) in need of treatment. Administration of isolated fulvate fractions in accordance with the methods of the provided herein may be via any route that provides a desired therapeutically effective amount and outcome. In some embodiments, an isolated fulvate fraction is administered in a pharmaceutical composition that comprises a unit dose of the isolated fulvate fraction and a pharmaceutically acceptable carrier. For example, administration may be oral or parenteral (e.g., intravenous, subcutaneous, intramuscular), transdermal, transmucosal (including buccal, nasal, rectal, sublingual, and vaginal), by inhalation, or via an implanted reservoir in a dosage form. Depending on the intended mode of administration, the pharmaceutical formulation may be a solid, semi-solid, or liquid, such as, for example, a tablet, a capsule, a caplet, a liquid, a suspension, an emulsion, a gel, a lotion, a cream, a foam, an ointment, a suppository, a granule, a pellet, a bead, a powder, or the like, preferably in unit dosage form suitable for single administration of a precise dosage or suitable for multiple administration dosages. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995), which is incorporated herein by reference in its entirety.

As used herein, the term "therapeutically effective amount" means on amount of a composition comprising an isolated fulvate fraction which is capable of alleviating, relieving, preventing, ameliorating, or eliminating a disease state for which administration of the composition is indicated. In some embodiments, a therapeutically effective amount includes administration of an amount of isolated fulvate fraction of 5, 10, 20, 30, 40, 50 60, 70, 80, 90, 100, 110, 120, 130, 140, 150, 160, 170, 180, 190, or 200 mg/kg or within a range defined by any two of the aforementioned amounts to the subject in need. In some embodiments, the composition is formulated having 1, 2, 3, 4, 5, 6, 7, 8, 9, 10, 11, 12, 13, 14, 15, 16, 17, 18, 19, 20, 25, 30, 35, 40, 45, or 50 µg/mL of an isolated fulvate fraction, or within a range defined by any two of the aforementioned values. In some embodiments, the composition is formulated having from about 5% to about 65% w/v of isolated fulvate fractions. Thus, in some embodiments, the compositions includes about 5%, 10%, 15%, 20%, 25%, 30%, 35%, 40%, 45%, 50%, 55%, 60%, or 65% w/v or within a range defined by any two of the aforementioned values.

As used herein, "sublingual" means "under the tongue" and refers to administration of a substance via the mouth in such a way that the substance is rapidly absorbed via the blood vessels under the tongue. Sublingual formulations may be desirable because they bypass the hepatic first pass metabolic process and therefore provide better bioavailability, rapid onset of action, and higher patient compliance.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal, and vaginal mucosa.

As used herein, a "transdermal drug delivery system" refers to a system or device for administration of a composition that releases drug upon application to the skin (or any other surface noted above). A transdermal drug delivery system may comprise a drug-containing layer, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. As described below, in one embodiment, the transdermal drug delivery system comprises a drug-containing polymer matrix that comprises a pressure-sensitive adhesive or bioadhesive, and is adopted for direct application to a user's (e.g., a subject's) skin. In other embodiments, the polymer matrix is non-adhesive and may be provided with separate adhesion means (such as a separate adhesive layer) for application and adherence to the user's skin.

It has been unexpectedly discovered that in some embodiments, the mode of administration provides for a substantially greater delivery of the compositions herein. Thus, in some embodiments, the mode of administration provides 2, 3, 4, 5, 6, 7, 8, 9, 10, 15, 20, 25, 30, 35, or 40 or greater times faster delivery of the compositions described herein as compared to normal delivery. In some embodiments, the transdermal delivery of the isolated fulvate fractions provides about 2, 3, 4, 5, 6, 7, 8, 9, 10, 15, 20, 25, 30, 35, or 40 or greater times faster delivery. In some embodiments, transdermal delivery of isolated fulvate fractions provides from about 20 to about 30 times faster delivery as compared to normal delivery.

There is considerable interest in the skin as a site of drug application both for local and systemic effect. However, the skin, and in particular the stratum corneum, poses a formidable barrier to drug penetration thereby limiting topical and transdermal bioavailability. Skin penetration enhancement techniques have been developed to improve bioavailability and increase the range of drugs for which topical and transdermal delivery is a viable option. Provided herein are enhancement techniques based on drug/vehicle optimization such as drug selection, prodrugs and ion-pairs, supersaturated drug solutions, eutectic systems, complexation, liposomes, vesicles, and particles. In some embodiments, enhancement may also take place via modification of the stratum corneum by hydration, chemical enhancers acting on the structure of the stratum corneum lipids and keratin, and partitioning and solubility effects.

The limitations on drug delivery caused by the barrier function of the skin have led to a search for methods of improving delivery of drugs through the stratum corneum. Various methods, including chemical or physical methods have been investigated. Chemical methods that have been utilized include adding ethanol or propylene glycol to drugs to enhance solubility. In some embodiments, the addition of from about 0.50% to about 7% by weight of M-007 to the formularies common in transdermal drug delivery system applications improved skin penetration, and delivery of the actives in the formularies by as much as about 350% when compared to non-enhanced formulas, and by as much as about 150% over those formularies using either ethanol, or propylene glycol as enhancement drug delivery methods.

The application of medications to the skin to ease ailments is a practice that has been utilized by humankind over the millennia and has included the application of poultices, gels, ointments, creams, and pastes. These applications were primarily intended for a local topical effect. However the use of adhesive skin patches to deliver drugs systemically is a relatively new phenomenon.

Transdermal drug delivery systems offer pharmacological advantages over the oral route and improved patient acceptability and compliance. As such, they have been an important area of pharmaceutical research and development over the last few decades. Some of the more common transdermal drug delivery systems ingredients and uses are listed in Table 1.

TABLE 1

Transdermal drug delivery system ingredients and uses

| Active Ingredient | Indication |
|---|---|
| Buprenorphine | Analgesia |
| Clonidine | Hypertension |
| Oestradiol | Hormone replacement |
| Oestradiol and Progesterone | Hormone replacement |
| Ethynyloestradiol, Norelgestromin | Contraception |
| Fentanyl | Analgesia |
| Glyceryl trinitrate | Angina |
| Hyoscine | Motion sickness |
| Lisuride | Parkinson's disease/restless leg syndrome |
| Nicotine | Smoking cessation |
| Testosterone | Hypogonadism |

Prior uses of transdermal delivery required that the drug be present in a high concentration within the patch for transdermal delivery to occur. The energy for drug release is derived from the concentration gradient existing between a saturated solution of drug in the system and the much lower concentration in the skin; drug movement occurs by diffusion. Since there is a high concentration within the patch and a low concentration in the blood, the drug will continue to diffuse, maintaining a constant concentration of drug in the circulation.

The rate of permeation across the skin is given by:

$$\frac{dm}{dt} = \frac{DCoP}{h}$$

Where D is the diffusion coefficient, Co the constant concentration of drug in the patch, P the partition coefficient between the skin and bathing solution, and h the thickness of the skin.

The transdermal permeation is improved if the drug and/or carriers have the following properties, including a molecular weight<500 Da (thus, in some embodiments, M-007 fulvate has a molecular weight of less than about 500 Da, such as, for example 250-310 Da); affinity for both lipophilic and hydrophilic phases (thus, in some embodiments, isolated fulvate fractions are both lipophilic and hydrophilic in nature); a low melting point, which effects the release of drug (thus, in some embodiments M-007 is a bioactive ionic sol with a very low transient temperature); and a high potency, where the drug is effective at low dosage (thus, in some embodiments, M-007 is a very strong electrolyte, effective at low dosage rates). Accordingly, in some embodiments, the M-007 fulvate compositions have improved transdermal permeation. In some embodiments, M-007 is an amino acid based amphiphilic compound with an ester linked compartment that has demonstrated skin permeation enhancement in topical compositions and in transdermal patch formularies with very low toxicological consequences.

In some embodiments, the method of treating includes selecting a subject who is in need. Selecting a subject in need includes identifying a subject having one or more of the disorders, diseases, or wounds as described herein, and electing to administer treatment to said subject.

In some embodiments, the treatment alleviates or relieves a skin disorder. As described herein, the term "alleviate" or "relieve" refers to an improvement in the skin disorder, disease, or wound. In some embodiments, an improvement includes an enhancement of the visual and/or sensory aspects of the superficial layers of the epidermis, as a result in the healing of the skin disorder, disease, or wound.

In some embodiments, the subject suffers from a skin disorder. In some embodiments, the subject suffers from pain. The pain can come from headaches, stomachaches, cancer, autoimmune disease, or a genetic disorder. In some embodiments, the pain is derived from a skin irritation, skin inflammation, systemic issues such as pain arising from joints, muscles, organs, and other sites of inflammation.

In some embodiments, the subject suffers from inflammation. In some embodiments, the subject suffers from inflammation. In some embodiments, the inflammation is on the skin, scalp, nasal passages, mouth, nail area such as the cuticles, eyes, vaginal area or the perineal area.

In some embodiments, the subject has a skin disorder. In some embodiments, the skin disorder is acne, alopecia, alopecia areata, alopecia totalis, angioma, athletes foot, Bowen's disease, carbuncles, candidiasis, cellulitis, dermatitis, eczema, atopic dermatitis, contact dermatitis, seborrhoeic dermatitis, stasis dermatitis, dermatofibroma, ecthyma, epidermolysis bullosa, erythrasma, folliculitis, Hidradenitis suppurativa, hives, hyperhidrosis, ichthyosis, impetigo, Kaposi's sarcoma, keloid, keratoacanthoma, keratosis, keratosis pilaris, keratosis follicularis, lichen planus, melanoma, melisma, miliaria, pediculosis, pemphigus, pityriasis rosea, pityriasis rubra pilaris, psoriasis, Raynaud's disease, ringworm, rosacea, scabies, scleroderma, sebaceous cyst, skin cancer, skin tags or shingles. In some embodiments, the subject is suffering effects of skin aging. In some embodiments, the effects of skin aging may include, for example, wrinkling of skin, sun spots, sagging, and loss of skin collagen. In some embodiments, the subject suffers from a skin disease or disorder such as acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidalis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes files, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminates faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne, psoriasis, including plaque psoriasis, guttate psoriasis, inverse psoriasis, pustular psoriasis, erythrodermic psoriasis, nail psoriasis, psoriatic arthritis, or combinations and variations thereof.

In some embodiments, the subject in need suffers from a skin disorder or a subject having a skin disorder is selected to receive a therapeutic. In some embodiments, the therapeutic is retin A, hydroquinone, retinol, or an antifungal. In some embodiments, the subject in need suffers from cancer or a subject having cancer is selected to receive an anticancer therapy. In some embodiments, the subject is selected to receive an analgesic.

As described herein, the composition including an isolated fulvate fraction can be a topical formulation. The topical formulation can further include, for example, a pharmaceutical vehicle that does not interfere with the function and viability of the isolated fulvate fraction. The "pharmaceutical vehicle" as described herein refers to an inert substance with which a medication is mixed to facilitate measurement and administration of the topical formulation.

In some embodiments, the active ingredients and mixtures of active ingredients can be used, for example, in topical formulations including a pharmaceutically acceptable carrier prepared for storage and subsequent administration. As used herein, "topical" refers to the administration or application of a formulation to the skin or various body orifices. Some embodiments include use of the titivate fractions described herein in combination with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives and stabilizers can be provided in the topical formulation. Preservatives can be used to keep the nutrients for the skin cells from breaking down. As used herein, the terms "carrier or diluent" may be a solid carrier or diluent for solid formulations, a liquid carrier or diluent for liquid formulations, or mixtures thereof. Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. For liquid formulations, such as for topical or parenteral formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Topical formulations including an isolated fulvate fraction can be formulated and used as a liquid, lotion, or a cream for topical application. Suitable ingredients in the topical formulation can include a for example, water, saline, dextrose, mannitol, lactose, lecithin, albumin, or sodium glutamate, and the like. If desired, absorption enhancing preparations (for example, liposomes), can be utilized.

As used herein, the term "injectable composition" refers to a formulation that is prepared for administration by injection. These injections may be administered by such routes as intravenous, subcutaneous, intradermal, intramuscular, intraarticular, or intrathecal.

In some embodiments, the pharmaceutical vehicle is soybean, grapefruit or almond oils, or synthetic fatty acid esters, such as ethyl oleate or triglycerides, or liposomes.

Coconut oil, olive oil, sesame oil, peanut oil, and soya can be used as suspension agents or lubricants in the topical formulation.

The topical formulation including an isolated fulvate fraction can further include, for example, one or more solvents, at least one botanical, and/or at least one emollient.

Table 2 provides a partial list of growth factors used to accelerate the repair of chronic wounds in humans. Table 3 provides results of double-blind, placebo controlled trials of growth factors and chronic wounds.

TABLE 2

Partial list of growth factors used to accelerate the repair of chronic wounds in humans

| Factor | Cell or Tissue of Origin | Selected Target Cells or Tissue | Selected Stimulatory (S) or Inhibitory (I) Actions | Clinical Trials |
|---|---|---|---|---|
| EGF | macrophages, monocytes | epithelium, endothelial cells | S: proliferation of keratinocytes, fibroblasts; and endothelial cells; keratinocyte migration | venous ulcers |
| FGF | macrophages, monocytes, endothelial cells | endothelium, fibroblasts, keratinocytes | S: proliferation of keratinocytes, fibroblasts, and endothelial cells; chemotaxis, ECM | diabetic; pressure, and venous ulcers |
| GM-CSF | macrophages, fibroblasts, endothelial cells | hematopoietic, inflammatory cells, neutrophils, fibroblasts | S: IGF-1 production | venous and arterial ulcers |
| HGH | pituitary gland | hepatocytes, bone, fibroblasts | S: IGF-1 production | venous ulcers |
| IL-1 | lymphocytes, macrophages, keratinocytes | monocytes, neutrophils, fibroblasts, keratinocytes | S: monocytes, neutrophils; macrophage chemotaxis | pressure ulcers |
| PDGF | platelets, macrophages, neutrophils, smooth muscle cells | fibroblasts, smooth muscle cells | S: proliferation of smooth muscle cells and fibroblasts; chemotaxis; ECM, contraction | diabetic and pressure ulcers |
| TGF-β | platelets, bone, most cell types | fibroblasts, endothelial cells, keratinocytes. lymphocytes, monocytes | S: ECM, fibroblast, activity, chemotaxis; I: proliferation of keratinocytes and endothelial cells | venous and pressure ulcers |

EGF = epidermal growth factor; FGF = fibroblast growth factor; GMCSF = granulocyte-macrophage colony-stimulating factor; HGH = human growth hormone; IL-1: interleukin-1; IGF-1 = insulin growth factor-1; PDGF = platelet-derived growth factor; TGF-β = transforming growth factor-β.

TABLE 3

Double-blind, placebo controlled trials of growth factors and chronic wounds

| Growth Factor | Authors | Target Wound Type (n) | Growth Factor Dose | Results |
|---|---|---|---|---|
| EGF | Falanga et al. | venous (44) | 10 μg/mL twice per day | N.S. |
| HGH | Rasmussen et al. | venous (37) | 1 IU/cm$^2$ per week | N.S. |
| GM-CSF | da Costa et al. | venous + arterial (25) | 400 μg injected once around the wound | N.S. |
| TGF-β2 | Robson et al. | venous (36) | 2.5 μg/cm$^2$ three times per week | N.S. |
| PDGF-BB | Robson et al. | pressure (20) | 1, 10, and 100 μg/mL daily | N.S. |
| PDGF-BB | Mustoe et al. | pressure (45) | 1 and 3 μg/mL daily | N.S. |
| PDGF-BB | Steed et al. | diabetic (118) | 2.2 μg/cm$^2$ daily | $p = 0.01$ |
| PDGF-BB | Wieman et al. | diabetic (382) | 30 and 100 μg/gm daily | $p = 0.007$ for 100 μg dose |
| bFGF | Richard et al. | diabetic (17) | 0.25 to 0.75 μg/cm$^2$ daily | N.S. |
| bFGF | Robson et al. | pressure (50) | 1, 5, and 10 μg/cm$^2$ | N.S. |
| IL-1B | Robson et al, | pressure (25) | 0.01, 0.1, and 1 μg/cm$^2$ daily | N.S. |

EGF = epidermal growth factor; HGH = human growth hormone; GMCSF = granulocyte-macrophage colony-stimulating factor; TGF-β 2 = transforming growth factor-β2; PDGF-BB = platelet-derived growth factor BB; bFGF = basic fibroblast growth factor; IL-1B = interleukin-1B; N.S. = not statistically significant.

VEGF is a signaling protein that promotes the growth of new blood vessels. VEGF forms part of the mechanism that restores the blood supply to cells and tissues when they are deprived of oxygenated blood due to compromised blood circulation.

HGF gene encodes a protein that binds to the hepatocyte growth factor receptor to regulate cell growth, cell motility, and morphogenesis in numerous cell and tissue types. This protein is secreted by mesenchymal cells and acts as a multi-functional cytokine on cells of mainly epithelial origin. This protein also plays a role in angiogenesis, tumorigenesis, and tissue regeneration. Human HGF is expressed as a linear, polypeptide-precursor glycoprotein containing 697 amino acid residues. HGF regulates the chemotaxis of T cells into heart tissue. Binding of HGF by cMet, expressed on T cells, causes the upregulation of cMet, CXCR3, and CCR4 which in turn imbues them with the ability to migrate into heart tissue. HGF has been shown to interact with the protein product of the C-Met oncogene, identified as the HGF receptor (HGFR). Both overexpression of the Met/HGFR receptor protein and autocrine activation of Met/HGFR by simultaneous expression of the hepatocyte growth factor ligand have been implicated in oncogenesis.

KGF is also known as FGF-7 and heparin-binding growth factor-7 (HBGF-7). KGF is a member of the fibroblast growth factor family and has been found to stimulate hair growth. When applied directly to the scalp, KGF binds to KGF receptors on the cell surface, acting as both a growth and survival factor by stimulating epithelial cell proliferation, differentiation, and migration and promoting a number of cell protective mechanisms, thereby stimulating hair growth and increasing the health of the skin. This behavior is especially beneficial to those persons that experience hair loss due to the effects of aging or the side effects of chemotherapy.

Cells that respond to KGF do so because they have receptors on the cell membrane that recognize the growth factor, normally produced by cells near or far from the target cell. The binding of KGF to the receptor initiates a cascade of molecular events that will eventually lead, among other effects, to cell division. KGF has been shown to regulate proliferation and differentiation in epithelial tissues and may regulate the stem cells of the hair follicle.

In some embodiments, the topical formulation further includes, for example, at least one growth factor. In some embodiments, the at least one growth factor is epidermal growth factor (EGF), platelet derived growth factor (PDGF), fibroblast growth factor (FGF), transforming growth factors (TGF-α and TGF-β), nerve growth factor (NGF), erythropoietin (EPO), insulin-like growth factors (IGF-I and IGF-II), interleukin cytokines (IL-1α, IL-1β, IL-2, IL-3, IL-4, IL-5, IL-6, IL-7, IL-8, IL-9, IL-10, IL-11, IL-12, IL-13), interferons (IFN-α, IFN-β, and IFN-γ), tumor necrosis factors (TNFα and TNF-β), colony stimulating factors (GM-CSF and M-CSF). Examples of growth factors (GFs) are described in U.S. Pat. No. 8,518,879 issued Aug. 27, 2013 and U.S. Pat. No. 9,119,974 issued Sep. 1, 2015, both incorporated by reference in their entirety herein.

In some embodiments, the topical formulation further includes one or more bioactive fragmented peptide. In some embodiments, the bioactive fragmented peptide is a collagenase-derived biologically active fragment, a tigerinin-based peptide, or combinations thereof. In some embodiments, the bioactive fragmented peptide is a salamander skin peptide, such as a tylotoin-based peptide. In some embodiments, the fragmented peptide is a frog skin peptide, such as a tigerinin-based peptide.

In some embodiments, the topical formulation can include at least one thickener, at least one humectant, and/or at least one preservative. Thickeners can include, for example, triglycerides, palmitates, myristates, stearates, polyethylene glycol, vegetable-based fatty alcohols, copolymers, cellulose gum, or xanthan gum. Humectants can be used for their moisturizing capabilities. Without being limiting, humectants can include but are not limited to sodium PCA, nanolipid gels, glycerin, alpha-hydroxy acid, butylene glycol, propylene glycol, hexylene glycol, sorbitol, hyaluronic acid, urea, glyceryl triacetate, neoagarobiose, glycerol, xylitol, maltitol, polymeric polyols, polydextrose, quillaia, MP diol, seaweed and algae extracts, and lactic acid.

In some embodiments, the topical formulation further includes at least one preservative. Without being limiting, preservatives can include benzoin resin, jojoba, vitamin E, alcohol, phenoxyethanol, methylparaben, propylparaben, diazolidinyl urea, sorbic acid, and triclosan. In some embodiments, the at least one preservative is benzoin resin, jojoba, vitamin E, alcohol, phenoxyethanol, methylparaben, propylparaben, diazolidinyl urea, sorbic acid, and/or triclosan.

Without being limiting, the formulation as described herein, can be within a lotion, a cream, a gel, a cosmetic (make-up), sunscreen or a sunblock. Make-up which can contain the formulation can include but is not limited to foundation, blush, BB cream, CC cream, foundation primer, primer, lipstick, lip gloss, eyelash primer, eyeshadow, cream eyeshadow, cream foundation, skin serum, and concealer.

When methods of treating a subject is required, for example, when the subject has inflammation on the scalp, the formulation can be provided in a shampoo, a conditioner, a hairspray, a mousse, a gel, or a hair rinse.

When methods of treating a subject is required, for example, when the subject has inflammation on the nails or surrounding cuticle region, the formulation can be provided in a gel, a lotion, a cream, or a cuticle oil.

When methods of treating a subject is required, for example, when the subject has inflammation nasal passages or surrounding area, the formulation can be provided as a nasal spray or nasal drops.

When methods of treating a subject is required, for example, when the subject has inflammation in the mouth or oral area such the gums lip, inner cheeks or roof of the mouth, the formulation can be provided as a mouth wash, toothpaste, a prophylactic paste, a tooth polish, a dental solution, an oral spray, dental floss, chewing gum, a lozenge, tablet, mouth rinse, or gel/cream within a teeth tray.

When methods of treating a subject are required, for example, when the subject has inflammation in the perineal area, the formulation can be provided as a suppository, cream, gel, ointment, or a lotion.

When methods of treating a subject is required, for example, when the subject has inflammation in the ear or surrounding areas of the ear, the formulation can be provided as medication formulated for the ears such as ear drops.

When methods of treating a subject is required, for example, when the subject has inflammation in the eye or surrounding areas of the eye, the formulation can be provided as medication formulated for the eyes such as eye drops, eye ointments or eye cream. In some embodiments, when the roots of the eyelashes are affected by inflammation, the formulation can be used in an eyelash primer, and the eyelash primer may be administered with a mascara brush or a small brush against the lash line.

When methods of treating a subject are required, for example, when the subject has inflammation of the vaginal area, the formulation can be provided as a cream, gel, ointment, lotion, or vaginal suppository.

A patient suffering from a skin disorder can be treated with an isolated fulvate fraction alone or in combination with other therapies known to treat the disease or condition, or alone or in combination with one or more growth factors and/or one or more bioactive fragmented peptides. As used herein, "therapy" includes but is not limited to a known drug. In addition, isolated fulvate fractions described herein can be combined with a drug associated with an undesirable side effect. By combining an isolated titivate fraction with such a drug, the effective dosage of the drug with the side effect can be lowered to reduce the probability of the side effect from occurring.

In some embodiments are provided methods of treating a patient diagnosed with a skin disorder or presenting with a skin disorder with a therapeutically effective amount of an isolated fulvate fraction, including administering said an isolated fulvate fraction to said patient such that the skin disorder is ameliorated or reduced. Embodiments include methods of treating a patient diagnosed with a skin disorder or presenting with a skin disorder with a therapeutically effective amount of an isolated fulvate fraction, including administering said isolated fulvate fraction to said patient such that the symptoms of the skin disorder are reduced or inhibited. In one embodiment, the isolated fulvate fraction functions by accelerating healing functions, including catalyzing the dynamic processes of wound healing. These processes include: an inflammatory reaction stage consisting of the extravasation of blood constituents with resultant platelet aggregation, blood coagulation, and migration of inflammatory cells to the wound site; a proliferative phase involving the migration and proliferation of keratinocytes, fibroblasts, and endothelial cells, leading to re-epithelialization and granulation tissue formation; and a tissue remodeling phase restoring tissue structural integrity and functional competence.

In some embodiments is provided methods of treating skin disorders with an isolated fulvate fraction as described herein, alone, in combination with growth factors, bioactive fragmented peptides, skin treatments, or in combination with wound or skin therapy by methods known in the art, such as with physical therapy, with pain management treatments, or with other treatments or therapies in the art.

Pharmaceutical Formulations

The pharmaceutical compositions of the present disclosure may include an effective amount of an isolated fulvate fraction of the present disclosure in combination with a pharmaceutically acceptable carrier. The compositions may further include one or more growth factors, as described herein, one or more bioactive fragmented peptide, as described herein, or combinations thereof. The compositions may further include other known drugs suitable for the treatment of skin disease or a wound. An effective amount of an isolated fulvate fraction of the present disclosure is an amount that ameliorates the disorder, or which causes the acceleration of the healing process, compared to that which would occur in the absence of an isolated fulvate fraction treatment. The effective amount (and the manner of administration) will be determined on an individual basis and will be based on a consideration of the subject (size, age, general health), the severity of the condition being treated, the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds described herein can be determined using in vitro tests, animal models or other dose-response studies, as are known in the art. The isolated fulvate fraction of the present disclosure can be used alone or in conjunction with other therapies. The therapeutically effective amount may be reduced when an isolated fulvate fraction is used in conjunction with another therapy.

The pharmaceutical compositions of the disclosure may be prepared, packaged, or sold in formulations suitable for intradermal, intravenous, subcutaneous, oral, rectal, vaginal, parenteral, intraperitoneal, topical, pulmonary, intranasal, buccal, ophthalmic, intrathecal, epidural, or another route of administration. The compounds may be administered by any convenient route, for example by infusion or bolus injection, by absorption through epithelial or mucocutaneous linings (e.g., oral mucosa, rectal, and intestinal mucosa, etc.), and may be administered together with other biologically active agents. Administration can be systemic or local. For example, the pharmaceutical compositions of the disclosure can be administered locally to a tumor via microinfusion. Further, administration may be by a single dose or a series of doses.

For pharmaceutical uses, an isolated fulvate fraction treatment of the present disclosure may be used in combination with a pharmaceutically acceptable carrier, and can optionally include a pharmaceutically acceptable diluent or excipient.

The present disclosure thus also provides pharmaceutical compositions suitable for administration to a subject. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active compounds can alternatively be formulated or encapsulated in liposomes, using known methods. Other contemplated formulations include projected nanoparticles and immunologically based formulations.

Liposomes are completely closed lipid bilayer membranes which contain entrapped aqueous volume. Liposomes are vesicles which may be unilamellar (single membrane) or multilamellar (onion-like structures characterized by multiple membrane bilayers, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase.

Methods of Administration

Some embodiments also encompass methods for making and for administering the disclosed topical formulations. Such disclosed methods include, among others, administration through topical administration, in which the administration includes administration as an aqueous suspension, an oily preparation or the like or as a salve, ointment or the like, as deemed appropriate by those of skill in the art for bringing the compositions into optimal contact with living tissue; and administration via controlled released formulations.

As will be readily apparent to one skilled in the art, the useful dosage to be administered will vary depending upon the age, weight size of the area to be treated, the particular ingredients employed, and the specific use for which these ingredients are employed.

Methods of Treatment
Skin, Hair, and Nail Care

The embodiments provided herein can be used in the treatment of subjects in need. In an exemplary embodiment, the topical formulation are used to treat spots, wrinkles, texture, pores, UV spots, brown spots, red areas of the skin, and porphyrins. As described herein, the porphyrins are the result of dead bacteria in the skin. The measurement of porphyrins is a measure of skin improvement as it relates to the propensity for breakouts or acne in the skin.

Additionally, the embodiments described herein can be used for treatment of the nails and diseases that can affect hair health. Nail diseases can include but are not limited to paronychia, fungal infection, onychatrophia, and nail psoriasis. Diseases can also be treated that affect hair health. Diseases that affect hair health can include but are not limited to alopecia, male pattern baldness (androgenic alopecia), hirsutism, hair shaft disorders, and ringworm.

In some embodiments, a method for treating a subject suffering from a skin disorder is provided. The method can include providing the isolated fulvate fraction of any of the embodiments described herein or the topical formulation of any of the embodiments described herein and applying the isolated fulvate fraction or topical formulation to the subject. In some embodiments, the isolated fulvate fraction or topical formulation is applied onto skin. In some embodiments, the skin disorder is selected from a group consisting of psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, and impetigo. In embodiments, the skin disorder arises from an autoimmune disorder. In some embodiments, the autoimmune disorder is Alopecia areata, autoimmune angioedema, Autoimmune progesterone dermatitis, Autoimmune urticarial, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis aceta, Mucha-Habermann disease, Psoriasis, Systemic scleroderma or Vitiligo. In some embodiments, skin diseases and skin disorders can include acne aestivalis (Mallorca acne), acne conglobate, acne cosmetics (cosmetic acne), acne fulminans (acute febrile ulcerative acne), acne keloidalis nuchae (acne keloidalis, dermatitis papillaris capillitii, folliculitis keloidalis, folliculitis keloidalis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminates faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphederma), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosiss syndrome (SAPHO syndrome), steroid rosacea, tar acne, skin cancer, tropical acne, plaque psoriasis, guttate psoriasis, inverse psoriasis, pustular psoriasis, erythrodermic psoriasis, nail psoriasis, and psoriatic arthritis.

The isolated fulvate fraction or topical formulations as described in the embodiments herein can be applied to the afflicted site one, two, three, four, or more times a day. In some embodiments, the topical formulation is within a serum for the skin, hair product, scalp, or nail product. The topical formulations in the embodiments herein can be used in a variety of personal care items such as, for example, soap, lotion, shampoo, conditioner, toner, or skin cream. As needed, the product can be made into serums for skin, hair products, nail products, and a variety of personal care items from soaps to shampoos. As described herein, the topical formulation can be used in perpetuity.

In treatment of the nails and cuticle region, the formulation can be a cream, gel, ointment, cuticle cream or a lotion. In a treatment for improving the health of the scalp or hair, the formulation can be within a shampoo, scalp cream or lotion, gel, spray formulation, mousse, or hair rinse.

In some aspects a method of treating a subject suffering from pain is provided. The method can include providing a composition of any of the embodiments provided herein or the topical formulation of any of the embodiments provided herein and applying the composition or topical formulation to the subject. In some embodiments, the composition or topical formulation is applied onto skin. In some embodiments, the pain is from arthritis. In some embodiments, the pain is from a disease. In some embodiments, the pain is from inflammation.

Oral Health

In some aspects a method of improving oral health is provided. Declining oral health can occur due to advancement of specific diseases or mechanical reasons as well, such as rough brushing of the teeth near the gum line, or lack in proper maintenance of the teeth and gum regions. Gum diseases can also occur as a result of improper care of diabetes, genetics, heart disease, pregnancy, Sjögren's syndrome, HIV/AIDS, dry mouth (xerostomia), oral cancer, saliva and salivary gland disorders in which the dry mouth can lead to problems with the gums and tissues, drug use, methamphetamine use, cocaine use, heroin use, smoking, and chewing tobacco. Aside from rough brushing near the gum line, diseases can also cause thinning and receding of the gum line.

In some embodiments described herein, formulations described herein can be used in the treatment of the gum line or tissues within the oral cavity. The formulation can include the isolated fulvate fraction isolated, purified, or extracted by the methods of any of the embodiments described herein or the isolated fulvate fraction of any of the embodiments described herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007.

The formulation can be provided within toothpaste, tooth gel, a mouth rinse, or a mouth wash. The administering can be performed two or three times a day. In some embodiments, the treatment is done for 1, 2, 3, 4, 5, 7, 15, 21, or 28 days any number of days in between any two aforementioned values.

In some embodiments described herein, formulations described herein can be used in the treatment of the gum line or tissues within the oral cavity. In some embodiments, a method of treating a subject suffering bad oral health is provided. The method can include administering the formulation to the subject need. In some embodiments, the administering is performed by placing the formulation in a dental tray and applying the tray to the upper and lower set of teeth such that the gums are saturated in the formulation. In some embodiments, the trays are worn for 1, 2, 3, 4, 5, 10, 15, 20, 30, 35, 40, 56, 50, 55, or 60 minutes or any other amount of time in between two aforementioned values. In some embodiments, the administering is performed two or three times a day. In some embodiments, the treatment is done for 1, 2, 3, 4, 5, 6, 7, 15, 21, or 28 days any number of days in between any two aforementioned values. In some embodiments, the subject in need has diabetes, a genetic disease, heart disease, Sjögren's syndrome, HIV/AIDS, dry mouth (xerostomia), oral cancer, or saliva and salivary gland disorders. In some embodiments, the subject is pregnant. In some embodiments, the subject has gum disease (periodontitis).

In some embodiments, the formulation is a toothpaste, tooth gel, mouth rinse/wash, or a gargle formulation. In some embodiments, the administration is performed by using a toothbrush with the toothpaste or by rinsing the mouth with the formulation.

Nasal Care

Nasal health is important as the nasal passages are used to filter air for breathing and remove dust, germs, and irritants. The nasal passages also warm and moisten the air to keep the lungs and passages from drying out. The nasal passages also contain nerve cells that can help with the sense of smell as well as taste. Common problems that can affect the nose can include but are not limited to nasal polyps, nosebleeds, dry nose, and irritation caused by rhinitis, allergies, runny nose, bacterial infections, and illnesses.

In some embodiments described herein, formulations described herein can be used in the treatment of the nasal passages, in which the formulation is administered to the subject need. In some embodiments, the administering is performed by administering the formulation into the nasal pathway. The formulation can include the isolated fulvate fraction made by the methods of any of the embodiments described herein or the isolated fulvate fraction of any of the embodiments described herein. The isolated fulvate fraction can be extracted, purified, and isolated by a method of any of the described embodiments herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007. In some embodiments, the administering is performed two or three times a day. In some embodiments, the treatment is done for 1, 2, 3, 4, 5, 6, 7, 15, 21, or 28 days any number of days in between any two aforementioned values. In some embodiments, the formulation is administered as a nasal drop, a nasal spray or as a nasal rinse/wash. In some embodiments, the subject in need has to nasal polyps, nosebleeds, dry nose, and irritation caused by rhinitis, allergies, runny nose, bacterial nasal infections, or illnesses that can cause dry nasal passages.

Auditory Care

Auditory care can be required when a subject has inflammation in the ear, the ear canal and the surrounding tissues. Common irritants such as bacteria, viruses, mucus, and other skin conditions can lead to the inflammation of the ear. External irritations can also occur that can cause inflammation of the ear. For example, when water gets trapped in the ear canal, bacteria can spread which can then cause inflammation and pain. Inner ear inflammation can also occur following a viral infection such as flu or upper respiratory infection. The virus can then cause swelling of the balance organs leading to dizziness with or without pain during inner ear inflammation.

In some embodiments, a method of treating a subject suffering from an auditory inflammation or ear infection is provided. In some embodiments, the method includes providing the isolated fulvate fraction of any of the embodiments described herein or the topical formulation of any of the embodiments described herein and applying the isolated fulvate fraction or topical formulation to the subject. In some embodiments, the isolated fulvate fraction or topical formulation is applied into the ear. The topical formulation can include the isolated fulvate fraction made by the methods of any of the embodiments described herein or the isolated fulvate fraction of any of the embodiments described herein. The isolated fulvate fraction can be extracted, purified, and isolated by a method of any of the described embodiments herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007. In some embodiments, the formulation is in the form of ear drops, ear wash, or ear ointment.

Vaginal Inflammation

In some embodiments, a treatment is provided to a subject having inflammation or discomfort in the vaginal or vulvovaginal area. Symptoms can include but are not limited to irritation and/or itching of the genital area, inflammation of the vaginal or perineal area or pain. Causes can include but are not limited to disruption of the healthy microbiota, infections, yeast, bacteria or viruses. Pathogens that can cause irritation can include but are not limited to *Gardnerella*, gonorrhea, chlamydia, *Mycoplasma*, herpes, *Campylobacter*, or *Trichomonas vaginalis*. Irritation can also occur due to effects of diabetes, birth control, bad diet, tight clothing, use of antibiotics, hormonal vaginitis due to postmenopause or postpartum, or loss of estrogen. Irritants can also from condoms, spermicides, soaps, perfumes, and lubricants. Loss of estrogen or hormonal vaginitis can also lead to dryness of tissues.

In some embodiments, a topical formulation is provided. In some embodiments, the topical formulation includes the isolated fulvate fraction made by any of the methods described by the embodiments herein or the isolated fulvate fraction of any of the embodiments described herein. The topical formulation can include the isolated fulvate fraction made by the methods of any of the embodiments described herein or the isolated fulvate fraction of any of the embodiments described herein. The isolated fulvate fraction can be extracted, purified, and isolated by a method of any of the described embodiments herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007. In some embodiments, the topical formulation is in the form of a gel, cream, foam or vaginal suppository.

In some embodiments, a method of treating a subject suffering from irritation or inflammation of the vaginal area is provided. In some embodiments, the method includes providing the isolated fulvate fraction described in any of the embodiments herein or the topical formulation of any of the embodiments described herein and applying the isolated fulvate fraction or topical formulation to the subject. In some embodiments, the formulation is in a gel, cream, lotion, foam or vaginal suppository. In some embodiments, the formulation is applied onto the vaginal and perineal area. In some embodiments, the formulation is administered as a vaginal suppository. In some embodiments, the subject is suffering from vaginal dryness. In some embodiments, the subject is suffering from a bacterial, fungal, or viral infection. In some embodiments, the subject has diabetes.

Perineal Care

In some embodiments described herein, a subject is treated for irritation of the perineal area, irritation of the perineal area can include but is not limited to hemorrhoids, anal fissures, rectal fissures, fistulas and other types of rectal infections. Without being limiting, the causes of irritation can come from proctitis, inflammatory bowel disease, Crohn's disease, ulcerative colitis, solitary rectal ulcer, rectal carcinoma, childbirth and episiotomy.

In some embodiments, a formulation is provided for use in perineal care. The formulation can include the isolated fulvate fraction made by the methods of any of the embodiments described herein or the isolated fulvate fraction of any of the embodiments described herein. The isolated fulvate fraction can be extracted, purified, and isolated by a method of any of the described embodiments herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007. The formulation can be provided as a cream, ointment, gel or a suppository.

In some embodiments, a method of treating a subject suffering from irritation of the perineal area is provided. In some embodiments, the irritation is caused by hemorrhoids, anal fissures, rectal fissures, fistulas, and other types of rectal infections, proctitis, inflammatory bowel disease, Crohn's disease, ulcerative colitis, solitary rectal ulcer, rectal carcinoma, childbirth, and/or an episiotomy. The method can include providing the isolated fulvate fraction of any of the embodiments described herein or the topical formulation of any one of the embodiments described herein and applying the isolated fulvate fraction or topical formulation to the subject. In some embodiments, the isolated fulvate fraction or topical formulation is applied onto skin or the perineal area. In some embodiments, the formulation is provided as a suppository. In some embodiments, the administration is performed by insertion of the suppository. In some embodiments, the subject suffers from diabetes.

Ocular Care

Ocular care is necessary for those who are immunocompromised or for subjects who are exposed to bacteria and irritants on a regular basis. For example, contact users or those who suffer from allergies are known to be exposed to irritants on a regular basis. Top irritants of the eye can include but are not limited to bacteria or viruses which can lead to conjunctivitis, allergic triggers such as dust or pollen and dry eye syndrome.

In some embodiments described herein, a subject is treated for irritation of the eye and the surrounding region. Irritation of the eye area can include but is not limited to conjunctivitis, bacterial or viral infection, allergens or dry eye syndrome.

In some embodiments, a formulation is provided for use in eye care. The formulation can include the isolated fulvate fraction made by the methods of any of the embodiments described herein or the isolated fulvate fraction of any of the embodiments described herein. The isolated fulvate fraction can be extracted, purified, and isolated by a method of any of the described embodiments herein. The method can include providing an aqueous slurry including HOM. In some embodiments, the method includes applying the aqueous slurry including HOM to high pressure column fractionation to obtain fractionated samples. In some embodiments, the method further includes applying the fractionated samples to molecular sieving. In some embodiments, the method further includes isolating a fulvate fraction. In some embodiments, the fulvate fraction is M-007. The formulation can be provided as an eye wash, an eye cream or eye drops. In some embodiments, the roots of the eyelashes are affected by inflammation, the formulation can be used in an eyelash primer. In some embodiments, the eyelash primer is administered with a mascara brush or a small brush against the lash line.

In some embodiments, a method of treating a subject suffering from irritation of the eye. In some embodiments, the irritation is caused by an eye infection by bacteria or virus, allergens or from dry eye syndrome. The method can include providing the isolated fulvate fraction of any of the embodiments described herein or the topical formulation of any one of the embodiments described herein and applying the isolated fulvate fraction or formulation to the subject. In some embodiments, the formulation is administered as eye drops into the eye. In some embodiments, the roots of the eyelashes are affected by inflammation, the formulation can be used in an eyelash primer. In some embodiments, the eyelash primer is administered with a mascara brush or a small brush against the lash line.

Angiogenesis Promotion

Angiogenesis is the formation of new blood vessels from existing vessels, and is a key step in all types of wound healing from knee scrapes to venous stasis ulcers, pressure sores and diabetic foot ulcers. In order for tissues to be repaired, there must be an adequate blood supply bringing nutrients, oxygen, and signaling molecules to the site of the injury.

The bioactive fragmented peptides disclosed herein, and found in the M-007 fraction, promote wound healing through the growth of new blood vessels and epithelial tissue, such as skin. As provided herein, these wound-healing peptides increase angiogenesis in vitro by 300-400 percent. These results provide a better understanding of the mechanisms regulating wound healing and may lead to new topical therapies for acute and chronic wound healing. As described herein, specific bioactive peptides were identified that exist in the M-007 fraction. By creating combinations of several key peptide fragments coupled with M-007 fulvate, additional classes of wound-healing peptides can be synthesized that promote the fundamental response to injury-blood vessel formation and epithelialization. This is accomplished by infusing the peptides with various fulvic acid fractions, at varying concentrations. Upon contact, the collagenase enzyme derived from *Clostridium histolyticum* releases, producing biologically active fragments as peptides from extracellular mammalian proteins. These peptides are shown to stimulate the proliferation of capillary endothelial cells, and enhance microvascular remodeling in their own right.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

These Examples demonstrate that disruptions of the physical barrier generates a signal to the innate immune system and initiate responses that would prevent an impending invasion from surrounding microbes. Indeed, increased expression of cathelicidins and secretory leukocyte protease inhibitor (SLPI) were previously demonstrated following cutaneous injury. As described herein, growth factors are produced to stimulate the regeneration of wounded tissue after injury, and in combination with M-007 fulvate are inducers of antimicrobial peptides, as shown herein. The growth factor response ceases after regeneration of the tissue, when the physical barrier protecting against microbial infections is re-established.

As shown herein, M-007 fulvate alone or in combination with growth factors significantly improves wound healing. M-007 fulvate, IGF-I, and TGF-α also induce or enhance the expression of the antimicrobial peptides/polypeptides hCAP-18, hBD-3, NGAL, and SLPI in human keratinocytes. Furthermore, the fulvate fraction in combination with these growth factors have a synergistic/additive effect in inducing expression of some of these antimicrobial peptides/polypeptides. These growth factors are present in saliva and have long been thought to support the proliferation of cells in wounds when animals lick their wounds. The Examples provided herein indicate that these growth factors may also aid in the prevention of infections in the wound.

TGF-α is a central factor in wound healing, but it also has possible immunological functions. Indeed, as shown herein, TGF-α induced the expression of the same number of antimicrobial peptides/polypeptides as the pro-inflammatory cytokine IL-1.

The induction of antimicrobial peptides/polypeptides by M-007 and growth factors may explain the presence of these proteins/peptides in psoriasis and cutaneous injury. The peptides/polypeptides hCAP-18, SLPI, NGAL, and hBD-3 have been detected in psoriatic lesions, and hCAP-18 and SLPI are increased in wounds (cutaneous injury).

The IGF-I receptor and TGF-α are increased in the psoriatic epidermis and both IGF-I and TGF-α are expressed in wounds. In the last few years many studies have attempted to understand how in the course of infection bacteria and bacterial products induce the expression of antimicrobial peptides in epithelial cells. The generation of growth factors in inflamed lesions may contribute to this response. It is noteworthy that TGF-α is present and reportedly released from neutrophils, monocytes, and eosinophils recruited to the epithelia in the course of inflammation. Furthermore, the synthesis of TGF-α is induced in macrophages following exposure to LPS. Although antimicrobial peptides-polypeptides typically have a broad spectrum of antimicrobial activity, there are differences in their specificity. We found that the spectrum of antimicrobial peptides/proteins induced in human keratinocytes depends on the agonist (growth factor, cytokine) present. As a result, keratinocytes may respond to different pathological stimuli by different patterns of expression of antimicrobial effector molecules. This was true even for the structurally and genetically closely related β-defensins. Because of the different antimicrobial specificities of the peptides/polypeptides, the ability to vary the defensive repertoire may be of functional importance and is believed to be beneficiated by the exposure to M-007 fulvate. Their ability to generate a differentiated immune response also underscores the importance of the keratinocyte as an immunocompetent cell in the innate immune system.

Induction of antimicrobial proteins/peptides has been most thoroughly described in insects (*Drosophila*) herein referenced, where the principal inducers of antimicrobial peptide expression were molecules previously known to regulate growth and development. In higher animals both IGF-I and TGF-α have this as their major function. Conversely, the pro-inflammatory cytokines known to induce the expression of antimicrobial peptides, IL-1, and IL-6, have also been found to stimulate the growth of human keratinocytes and thus may also be considered growth factors. Thus, from insects to man the processes of growth and expression of antimicrobial peptides appear to be intertwined.

From the clinical point of view, identification of the role of growth factors as mediators of induced expression of antimicrobial peptides/polypeptides in human keratinocytes raises the possibility that these factors may be manipulated to increase the resistance of skin grafts to infection.

Experimental Materials and Methods

The following experimental materials and methods were used for the Examples described below.

StrataTest® Human Skin Research Model

The full-thickness StrataTest® human skin model is composed of both an epidermis and a dermis tissue for in vitro consumer product testing, drug discovery, and toxicity screening. It displays the same physical, chemical, and histological characteristics of human skin, and is supplied in a readily-available, easy-to-use 24-well test format. Many of today's animal and cell-based toxicity testing models are burdened by significant accuracy, reproducibility, cost, and ethical concerns. The unique characteristics of StrataTest® skin tissue provide not only an enhanced, high-quality in vitro testing model; they enable better prediction of in vivo biological responses than standard, two-dimensional, monolayer cultures. Unlike models that possess only an epidermal layer, the presence of both epidermal and dermal compartments permits paracrine signaling. The tissue grown in vitro in the StrataTest® plate grows precisely as new human skin grows in vivo, fully replicating its structure and function. Unlike cultured human keratinocytes from other sources, the uniquely uniform NIKS® cells can be grown indefinitely in the laboratory, resulting in less batch-to-batch variability. The StrataTest® human skin model offers consistent cell sourcing and quality, coupled with the faithful three-dimensional reproduction of native human skin. These characteristics provide customers with a highly-reproducible, accurate, and cost-effective measurement of the in vitro response to a broad range of chemicals, compounds, and other potential toxins.

SDS-PAGE and Immunoblotting

SDS-PAGE and immunoblotting were performed with Bio-Rad systems according to instructions given by the manufacturer (Bio-Rad, Hercules, Calif.). For immunoblotting, after the transfer of proteins from the 14% polyacrylamide gels, the polyvinylidene difluoride (PVDF) membranes (Millipore, Bedford, Mass.) were blocked for 1 h with 5% skimmed milk in PBS. For detection of hCAP-18, NGAL, and SLPI, the PVDF membranes were incubated overnight with primary antibodies. The following day, the membranes were washed and incubated for 2 h with alkaline phosphatase-conjugated secondary antibodies (DAKO, Glostrup, Denmark) then washed and visualized by 5'-bromo-chloro-indolyl phosphate (Sigma-Aldrich) and nitro blue tetrazolium (Sigma-Aldrich).

Extraction and Detection of Human β defensins (hBD-3)

Medium from keratinocytes was extracted with Macro-Prep CM Support beads (Bio-Rad) overnight at 4° C. The beads were subsequently washed and bound material was eluted with 30% acetic acid. The eluted material was dialyzed in 5% acetic acid and lyophilized before resuspension in sample buffer for acid urea (AU)-PAGE.

AU-PAGE and immunoblotting were performed according to instructions given by the manufacturer (Hoeffer, San Francisco, Calif.). After transfer of proteins from the 12.5% acrylamide gels, the PVDF membranes were fixed for 30 min in TBS with 0.05% glutaraldehyde (Sigma-Aldrich), followed by blocking with Superblock Blocking Buffer (Pierce, Rockford, Ill.). For visualization of hBD-3, the PVDF membranes were incubated overnight with primary antibodies. The following day, the membranes were incubated for 2 h with HRP-conjugated secondary antibodies, (Pierce) and visualized by Immun-Star HRP luminal/enhancer and Immun-Star peroxide buffer (Bio-Rad).

Growth and Stimulation of Keratinocytes

Cells were grown in serum-free keratinocyte medium from Clonetics (KGM-2 Bullet Kit; San Diego, Calif.) with bovine pituitary extract, transferrin, human epidermal growth factor (EGF), hydrocortisone, gentamicin, amphotericin B, and epinephrine, but without insulin. Cells were stimulated beginning 24 h after complete confluence was reached. Cells and medium was harvested 0, 3, 6, 12, 24, and 48 h after stimulation with IGF-I (100 ng/mL), TGF-α (50 ng/mL), TGF-β1 (10 ng/mL), hFGF (100 ng/mL), IGF-I/TGF-α, IL-1β (20 ng/mL), IL-6 (100 ng/mL), EGF (100 ng/mL), and INF-α (20 ng/mL). For demonstration of hCAP-18, medium and cells were harvested 0, 24, 48, 72, and 96 h after stimulation with IGF-I.

Organotypic Culture and Stimulation

Primary epidermal cultures EPI-200-3S (MatTek, Ashland, Mass.) containing human epidermal keratinocytes were grown on a collagen-coated Millicell CM membranes. The cultures were placed in 12-well plates with medium supplied by the manufacturer (which contains no bovine pituitary extract). On day 4 the epidermal cultures were lifted to the air-liquid interface and then cultured in air-liquid interface for another 4 days according to the instructions of the manufacturer. On day 2 after airlifting the cultures, the medium was changed to medium without insulin or EGF. On day 4 after airlifting the cultures were stimulated with IGF-I (100 ng/mL), TGF-α (50 ng/mL), or a combination of IGF-I and TGF-α. Cells were harvested after 48 h of stimulation.

RNA Isolation

Total RNA was isolated with TRIzol (Life Technologies, Gaithersburg, Md.) according to recommendations of the manufacturer. RNA was precipitated with ethanol and re-suspended in 0.1 mM EDTA. The concentration was determined by spectrophotometric measurement, and the integrity of the RNA assessed by running a sample on an agarose gel.

Northern Blotting

For Northern blotting, 5 µg of RNA was run on a 1% agarose gel with 6% formaldehyde dissolved in 1×MOPS for size separation. The RNA was transferred to a Hybond-N membrane (Amersham Pharmacia Biotech, Little Chalfont, U.K.) by capillary blotting and was fixed by UV irradiation. The filters were pre-hybridized for a minimum of 30 min at 42° C. in 10 mL of ULTRAhyb (Ambion, Austin, Tex.) and hybridized overnight at 42° C. after the addition of an additional 5 mL of ULTRAhyb containing the P-labeled probe. The membranes were washed twice for 5 min each time at 42° C. in 2×SSC (1×SSC=150 mM NaCl/15 mM sodium citrate, pH 7.0)/0.1% SDS, followed by twice for 15 min each time in 2×SSC/0.1% SDS, once for 15 min in 0.2×SSC/0.1% SDS, and once for 15 min in 0.1×SSC/0.1% SDS at 42° C. The blot was developed and quantified by a phosphorimager (Fuji Imager Analyzer BAS-2500, Image Reader version 1.4E, image Gauge version 3.01 software; Fuji, Stockholm, Sweden). The sizes of the mRNAs were determined by reference to 18S and 28S rRNA, which were visualized by ethidium bromide staining. The membranes were stripped by boiling in 0.1% SDS before re-hybridization.

The probes used for hybridization were cDNA fragments radiolabeled with [α-P]dCTP using the Random Primers DNA Labeling System (Life Technologies). The probes NGAL, hCAP-18, hBD-2, and β-actin have previously been described. The probes for SLPI, hBD-1, and hBD-3 were amplified from cDNA from keratinocytes with the following primers: SLPI, 5'-ATGAAGTCCAGCGGCCTC-3' (SEQ II NO: 1), and 5'-AAGAGAAATAGGCTCGTTTATTT-3' (SEQ ID NO: 2); hBD-1, 5'-GCTCAGCCTC-CAAAGGAGC-3' (SEQ ID NO: 3), and 5'-AAAAGAATGCTTATAAAAAGTTCAT-3' (SEQ ID NO: 4); and hBD-3, 5'-GGAATCATAAACACATTA-CAGAA-3' (SEQ ID NO: 5), and 5'-CGGGCAATCAT-AAACACATTACAGAA-3' (SEQ ID NO: 6). The probe for hBD-4 was amplified from genomic DNA using the following primers: 5' GCAGCCCCAGCATTATGCA-3' (SEQ ID NO: 7) and 5'-AAGCTACTGAGGTCCTACTTC-3' (SEQ II) NO: 8). PCR-amplified probes were cloned into plasmids and verified by DNA sequencing. The probes for labeling were liberated from the plasmids by restriction with suitable restriction enzymes. The digests were run on 1% agarose gels and the probes were purified by gel extraction before labeling.

Quantitation of Proteins

Human CAP-18 and NGAL were measured by ELISA as described previously. SLPI was measured by a sandwich ELISA using recombinant SLPI as standard.

Immunohistochemistry of primary keratinocytes was performed as follows. The cytospins were fixed for 10 min in 10% formalin in following stimulation with growth factors; cytospins were prepared from trypsinated PBS and subsequently washed with TBS. The slides were incubated with a 1/1000 dilution of rabbit polyclonal antibodies against NGAL and hCAP-18 and a 1/666 dilution of rabbit polyclonal antibodies against hBD-3. The antibodies was diluted in TBS with 1% gelatin, 0.05% Tween 20 (Sigma-Aldrich), and 0.01% thimerosal, and the slides were incubated for 24 h at room temperature. After three 20-min washes in TBS with 0.05% Tween 20, the slides were incubated with alkaline phosphatase-conjugated goat anti-rabbit IgG (Pierce) diluted 1/1000 in the same buffer as the first antibody and incubated for another 24 h, followed by three 20-min washes. Color was developed with Fast Red chromogen (Sigma-Aldrich) in Tris buffer, and the slides were counterstained with Harris hematoxylin (EM Science, Gibbstown, N.J.).

Example 1

Extraction and Isolation of Fulvate Fraction

This example demonstrates the method for extracting and isolating a fulvate fraction from humified organic matter.

Humified organic matter (HOM) is obtained from a deposit of peat, humin, leonardite, humilite, brown coal, river water, lake water, swamp residue, and rich organic muds. In particular, leonardite is high in fulvate fractions.

An efficient method for extracting and refining humates from organic lignite sources such as leonardite as the raw material is provided herein. The mined leonardite, generally appearing as overburden to various coal deposits is removed, and having moisture content of 43-50% is taken and air dried in a kiln to reduce the moisture level to 15-20% so that it can be used as raw material. It then pulverized to less than 8 mm using a Jet Mill Pulverizer. After which 5 to 30% of pulverized leonardite is mixed with 70 to 95% of solution containing 1 to 5% of potassium hydroxide. The contents are allowed to react at a range of temperature 60-80° C., for a period of approximately 2 to 6 hours with continuous stirring or as required, so that the material is in suspension. The required process temperature can be maintained by imbedded electric coil heaters, external steam heating, or other sources of heat generation that is non flame generated in contact with the solution itself. The pH (7 to 12) of the medium is to be adjusted continuously during the process, to obtain the desirable extract of humic sol. After the raw material digestion period the solution is to be agitated for uniform dispersion for 1 to 2 hours. It is then transferred to a settling column for separation of solids and sludge. After a period of time, generally from 24 to 48 hours a clear brown to amber colored solution is obtained. The solution is made up to a concentration of 2-4% and the pH corrected to 8 to 10.5. The solution is transferred to a main storage tank, at which time the residual unreacted leonardite and minerals, plus agglomerate portion is discarded.

The extracted liquid is further concentrated in a shell and tube evaporator to obtain a concentration of about 10-15% at a temperature of about 150° C. The concentrated solution is transferred to electrically heated/steam heated tray-dryer at 100 to 150° C. Vacuum atmosphere is maintained continuously to evacuate the vapor to obtain the desired dried product, which contains residual moisture of about 8-15%. The product obtained is black lustrous and fully water-soluble flake containing 50 to 70% humic acid (HA) with 13 to 18% of the humic being a fraction of fulvic acid (FA) and ulmic acids. This dry powdered concentrated humic acid is stored for further processing into various fractions. The HA/FA powder is put into solution using deionized water at a ratio of 5 pounds of HF/FA concentrate per 1 gallon of deionized water. The sol is heated to from 75 to 90° C. and is subjected to the addition of citric acid powder, added slowly until a pH of 4.7 is obtained. The adjusted 4.7 pH sol is stirred for from 1 to 5 hours at low speed, maintaining a temperature of 75 to 90° C. After the selected mixing and reaction time, the sol is transferred into a modified electric current induced column separator and let stand. A DC electric current is applied to the sol at a rate of 2.4 to 4.2 amps per square meter, which assists in the separation of the humic and fulvic acid fractions. After a 24 to 72 hour period a separation layer will appear showing a heavy dark brown to black substance at the column bottom (containing primarily ulmic acid) and a second layer of dark brown to medium brown sol being of a humic acid concentrate, followed by a top layer of light brown to yellow layer consisting of primarily fulvic acid. These individual layers are extracted and stored in appropriate containers for further use and/or processing.

The basic extracted fulvic acid has a molecular weight averaging from about 50 to about 1200 Da and a general chemical composition of the fulvic acid is as a chemically and biologically relatively stable polyelectrolyte with a number-average molecular weight of 951 (measured by vapor pressure osmometry) and contains 9.1 mequiv COOH, 3.3 mequiv phenolic OH, 3.6 mequiv alcoholic OH, and 3.1 mequiv C=O per g, Analysis (%) shows 50.90, C; 3.35, H; 0.75, N; 0.25, S; and 44.75, 0, with a molecular formula calculated from this data as $C_{12}H_{16}$—(COOH),(OH),(CO).

The extracted fulvic acid concentrate (EFAC) is further processed and purified by passing the supernatant designated "FA Extract 1" through a column of XAD-8 (0.15 mL of resin per gram of initial sample dry weight at a flow rate of 1.5 bed volumes per h). The eluent is discarded; the XAD-8 column containing sorbed fulvic acid is rinsed with 0.65 column volumes of distilled $H_2O$. The XAD-8 column is back eluted with 1 column volume of 0.1 M NaOH, followed by 2 to 3 column volumes of distilled 1120. The solution is immediately acidified with 6 M HCl to a pH of 1.0. Concentrated hydrofluoric acid (HF) added to a final concentration of 0.3 M HF. The solution volume should be sufficient to maintain the fulvic acid in solution. The supernatant designated "FA Extract 2" is then passed through a column of XAD-8 (1.0 mL of resin per gram of initial sample dry weight). The back elution and acidification steps as performed for "FA Extract 1" above, are repeated. The final eluates from each of the fulvic acid extracts are combined and passed through XAD-8 resin in a glass column (column volume should be one-fifth of sample volume). The column is rinsed with 0.65 column volumes of distilled $H_2O$, followed by back elution with 1 column volume of 0.1 M NaOH followed by two column volumes of distilled $H_2O$. The eluate is passed through $H^+$-saturated cation exchange resin (Bio-Rad AG-NIP-5 (Bio-Rad, Richmond, Calif.)) using three times the mole of Na ions in solution. The resulting eluate is freeze dried to recover the $H^+$-saturated fulvic acid.

As an alternative to purification using resin treatments, exhaustive dialysis against distilled $H_2O$ may be used. If there is a significant concentration of polyvalent cations such as $Al^{3+}$ present, these may form insoluble metal-humate complexes as the solution is neutralized. Therefore, the dialysis should be carried out against dilute HCl initially until the concentration of any polyvalent cations has been significantly reduced, before finally dialyzing against distilled $H_2O$. Technically, a fraction obtained in this way should be referred to as a fulvic fraction, rather than fulvic acid, as it is likely to contain significant amounts of unbound polysaccharide.

In order to select the fulvic molecular weight of known importance, differences in the molecular composition of fulvic acid by size fractions was detected by size-exclusion chromatography on line, via Fourier transform ion cyclotron resonance (FTICR) mass spectrometry.

Size-exclusion chromatography was coupled to electrospray ionization Fourier transform ion cyclotron resonance mass spectrometry SEC-FTICR-MS) to separate a fulvic acid isolate into three size fractions and to select the elemental composition of fulvic acids in these fractions. Molecular formulas of about 3000 ions in the mass range of 200-700 Da were derived, many of which occur in all three fractions and follow the same system of elemental composition. Product ion spectra generated by SEC coupled to quadrupole-time-of-flight-MS (Q-TOF-MS) confirmed that the ions of all three fractions are polycarboxylates with hardly any other functional moiety. However, SEC-FTICR-MS revealed that the ions generated from the high molecular weight (HMW) fraction are enriched in carboxyl groups and are more aromatic as compared with the low molecular weight (LMW) fraction. These findings support the idea that the HMW fulvic acids are formed from LMW fulvic acids. The shift in the relative frequency of ions from the LMW to the HMW fraction is in line with different interaction mechanisms: HMW fulvic acids may be aggregates held together by electrostatic interaction of the carboxylate groups via hydrogen bonds or with polyvalent cations or by hydrophobic interaction of their carbon backbone, or consist of LMW fulvic acids covalently bound to each other or to (aliphatic) alcohols. Based on these findings we have determined that the fulvic fraction having a weight of between 80 and 350 Da are more desirable in bio stimulation applications where strong cation exchanges are desirable and where chelation of minerals and metal substrates are desirable for nitrification of cell growth stimuli. In some embodiments, the M-007 molecule has a MW in the range of about 80 to 700 Da. In some embodiments, the molecular weight of M-007 is about 309 Da.

Example 2

Efficacy of the Fulvate Fractions

This example demonstrates that fraction M-007 is particularly bioactive and efficacious.

The fractions were tested to determine their efficacy, and it was found that M-007 is particularly useful as a therapeutic agent for cellular regeneration because it is small, cationic, highly active, and is effective in messenger, transport, and delivery mechanisms.

Example 3

Combinations of M-007 and Growth Factors

This example shows the therapeutic effects of combining M-007 with various growth factors.

Fibroblast growth factor-binding protein (FGF-BP) 1 is a secreted protein that can bind fibroblast growth factors (FGFs) 1 and 2. These FGFs are typically stored on heparin sulfate proteoglycans in the extracellular matrix in an inactive form, and it has been proposed that FGF-BP1 functions as a chaperone molecule that can mobilize locally stored FGF and present the growth factor to its tyrosine kinase receptor. FGF-BP1 is up-regulated in squamous cell, colon, and breast cancers and can act as an angiogenic switch during malignant progression of epithelial cells. FGF-1 and -2 interactions with recombinant human FGF-BP1 protein were investigated, and the effects on signal transduction, cell proliferation, and angiogenesis were ascertained. Recombinant FGF-BP1 specifically binds FGF-2 and this binding is inhibited by FGF-1, heparin sulfate, and heparinoids. Furthermore, FGF-BP1 enhances FGF-1- and FGF-2-dependent proliferation of NIH-3T3 fibroblasts and FGF-2-induced extracellular signal-regulated kinase 2 phosphorylation. Finally, in the chicken chorioallantoic membrane angiogenesis assay, FGF-BP1 synergizes with exogenously added FGF-2. We conclude that FGF-BP1 binds directly to FGF-1 and FGF-2 and positively modulates the biological activities of these growth factors. Using these findings as base lines we infused these proteins with fulvate and fulvate fractions, more specifically with M-007 fractions having a molecular weight of 309 Da in the following formularies, and treated human skin cell cultures, as indicated.

TABLE 4

Formularies of M-007 with growth factors

Percent of Wound Closure in Epidermal Human Skin Cell Culture

| Form. No. | Day 1 | Day 2 | Day 3 | Day 4 | Day 5 | Day 6 | Day 7 | Day 8 | Day 9 | Day 10 |
|---|---|---|---|---|---|---|---|---|---|---|
| 001 | 1.8 | 3.9 | 12.6 | 32.4 | 46.1 | 58.5 | 66.2 | 77.1 | 82.8 | 88.1 |
| 002 | 1.65 | 3.45 | 11.9 | 23.8 | 39.9 | 46.9 | 54.6 | 68.2 | 74.5 | 87.9 |
| 003 | 1.95 | 4.65 | 12.3 | 38.2 | 45.4 | 57.2 | 63.9 | 76.0 | 89.2 | 93.7 |
| 004 | 1.98 | 4.9 | 13.0 | 39.6 | 50.3 | 63.9 | 76.0 | 89.2 | 93.7 | 100 |
| 005 | 3.6 | 11.0 | 23.3 | 43.2 | 59.2 | 73.2 | 86.2 | 97.3 | 100 | — |
| 006 | 3.4 | 10.2 | 19.6 | 32.5 | 46.6 | 58.5 | 71.0 | 87.2 | 98.5 | 100 |
| 007 | 2.95 | 10.4 | 20.2 | 39.5 | 59.1 | 73.6 | 85.9 | 96.8 | 100 | — |

Formula Key
001=50% FGF-1 dispersed in a 5% saline solution and DI water
002=50% FGF-2 dispersed in a 5% saline solution and DI water
003=25% by weight M-007-1 in DI water
004=35% by weight M-007-2 in DI water
005=25% FGF-1+25% M-007-1 by fl. vol. in DI water
006=25% FGF-2+25% M-007-2 by fl. vol. in DI water
007=20% FGF-1+30% M-007-1 by fl. vol. in DI water Keratinocytes were stimulated with the growth factors involved in wound healing (IGF-I, TGF-α, TGF-β1, and bFGF) as well as with representative pro-inflammatory cytokines (IL-1β, IL-6, and TNF-α), and with M-007 fulvate. To avoid interference from growth factors already present in the medium, cells were grown in serum-free medium without insulin (insulin binds with low affinity to the IGF-I receptor) and with only 0.15 ng/mL EGF. It has previously been noted that keratinocytes must reach a certain level of differentiation to express antimicrobial peptides. A model was selected in which primary keratinocytes were grown to confluence, and then stimulated 24 later, because this gave consistent expression of the antimicrobial peptides/polypeptides following stimulation with growth factors and made a direct comparison to the M-007 treated keratinocytes.

The cathelicidin hCAP-18 was up-regulated by IGF-I at both the protein level (ELISA) and the mRNA level. A long time course of induction was chosen to demonstrate the accumulation of hCAP-18 in the medium. The presence of hCAP-18 in stimulated keratinocytes was further verified by Western blot and immunostaining with anti-hCAP-18 antibodies of stimulated and unstimulated keratinocytes.

Example 4

Combinations of M-007 and bFGF

This example details the ability of basic fibroblast growth factor (bFGF) to accelerate tissue repair in human epidermal cell cultures.

Figure 2A:
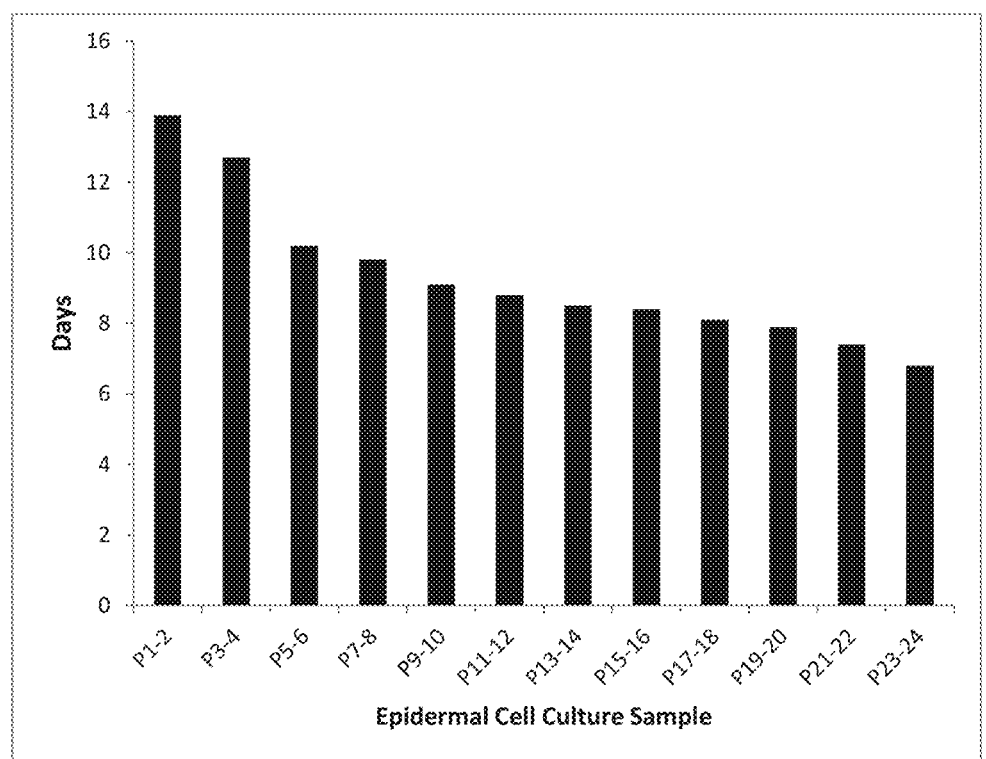
FIG. 2A shows the baseline wound healing for epidermal cell cultures in untreated control groups and varying treatment groups, Each treatment was repeated in duplicate, the graph depicts the average wound closure in number of days. Plates 1 and 2 (P1-2) untreated control; P3-4 treated with phosphate buffered saline; P5-6 treated with bFGF sol. No. 00373; P7-8 treated with bFGF sol. No. 00376; P9-10 treated with M-007 fulvate sol. No. 00321A; P11-12 treated with M-007 fulvate sol. No. 00321B; P13-14 treated with bFGF sol. No. 00373+M-007 fulvate sol. No. 00321A @70/30 ratio; P15-16 treated with bFGF sol. No. 00373+M-007 fulvate sol. No. 00321A @50/50 ratio; P17-18 treated with bFGF sol. No. 00373+M-007 fulvate sol. No. 00321A @30/70 ratio; P19-20 treated with bFGF sol. No. 00376+M-007 fulvate sol. No. 00321A @70/30 ratio; P21-22 treated with bFGF sol. No. 00376+M-007 fulvate sol. No. 00321A @50/50 ratio; P23-24 treated with bFGF sol. No. 00376+M-007 fulvate sol. No. 00321A @30/70 ratio.
Figure 2B:
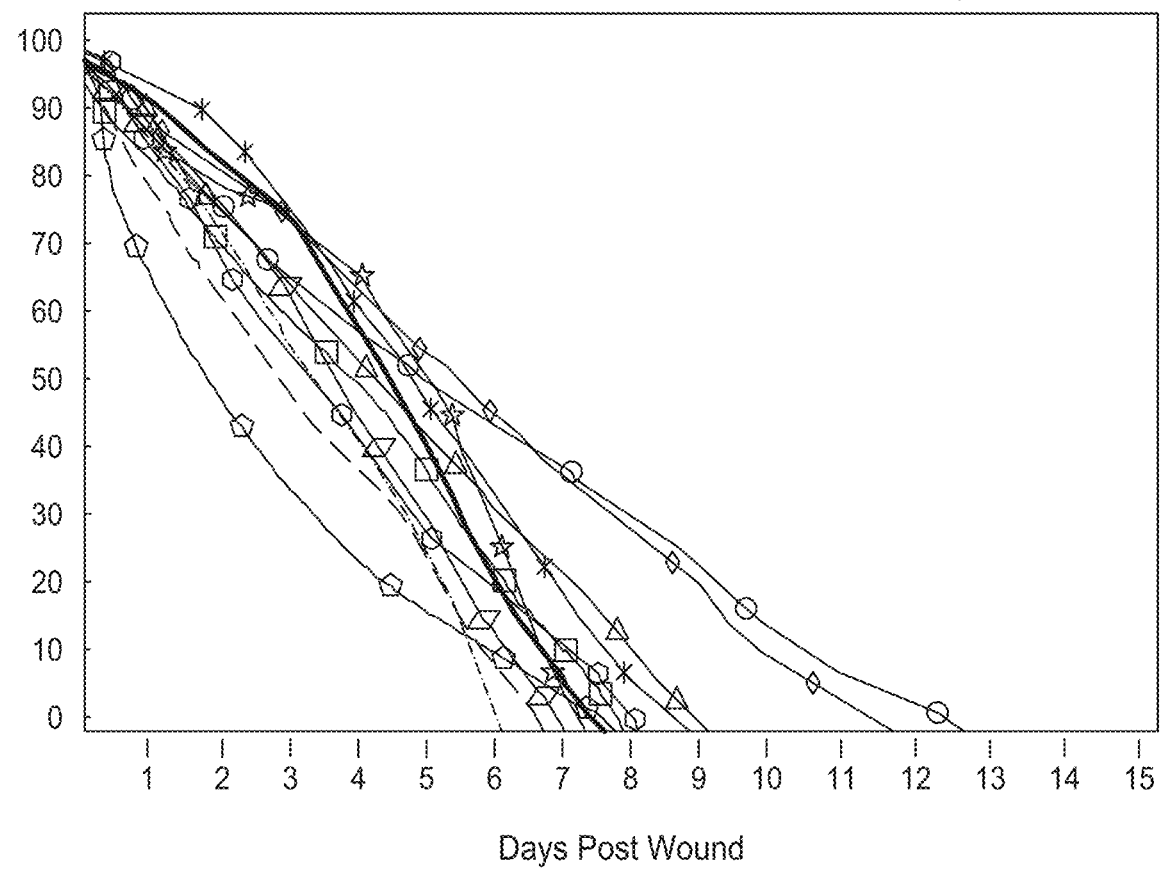
FIG. 2B depicts a graphical representation of the wound healing for the treatment groups described in FIG. 2A.

A 4-mm mucosal defect was surgically made in the CBA Epidermal Culture. The formulation Sol. of bFGF, M-007, and control saline was injected along the edge of the wound defect immediately after scratch. The control group received only phosphate-buffered saline vehicle.

bFGF and bFGF plus M-007 Fulvate significantly accelerated granular tissue formation and re-epithelialization. From the histologic analysis, both the bFGF and M-007 treated samples showed relatively faster collagen maturation, Starting three days after scratch/wound, fibroblast growth factor receptor 1 (FGFR1)-positive cells appeared in the granular and spinous cell layers of the re-epithelializing mucosa in the both the bFGF-M-007 treated samples, whereas almost none was observed in the intact oral mucosa. By day 5, FGFR1-positive cells were seen below the stratum corneum, even in the control group. However, the number and intensity of FGFR1-positive cells in the bFGF-treated group were greater than in the control group, and the bFGF plus M-007 treated group showed an increase of 75% over that of the bFGF alone, Results of immunostaining against proliferating cell nuclear antigen showed that bFGF plus M-007 Fulvate stimulated cell proliferation of the basal cell layer in the regenerating epithelium. At a higher dose of bFGF and M-007, proliferating cell nuclear antigen-positive cells were also observed in the submucosal connective tissue. The results of the baseline screening tests are shown in FIG. 2. FIG. 2 shows the number of days for wound closure post-wound. Each sample was repeated in duplicate, thus FIG. 2 represents the average of each sample. P1-2 are control plates 1 and 2 and are epidermal cell culture with no external treatment. P3-4 is epidermal cell culture treated with phosphate buffered saline only. P5-6 is epidermal cell culture treated with bFGF. P7-8 is epidermal cell culture treated with bFGF sol. No. 00376. P9-10 is epidermal cell culture treated with M-007 fulvate sol. No. 00321A. P11-12 is epidermal cell culture treated with M-007 fulvate sol. No. 0032113. P13-14 is epidermal cell culture treated with bFGF No. 00373+M-007 titivate sol. No. 00321A @ 70/30 ratio. P15-16 is epidermal cell culture treated with bFGF No. 00373+M-007 fulvate sol. No. 00321A 50/50 ratio, P17-18 is epidermal cell culture treated with bFGF No. 00373+M-007 fulvate sol. No. 00321A @ 30/70 ratio. P19-20 is epidermal cell culture treated with bFGF sol No. 00379+ M-007 fulvate sol. No. 00321A 70/30 ratio. P21-22 is epidermal cell culture treated with bFGF sol. No. 00376+ M-007 fulvate sol. No. 00321A @50/50 ratio. P23-24 is epidermal cell culture treated with bFGF sol. No. 00376+ M-007 fulvate sol. No. 00321A @30/70 ratio.

Optimal delivery of growth factors often requires complex engineered biomaterial matrices, which can face regulatory issues for clinical translation. To simplify delivery systems and render strategies more applicable, growth factors can be engineered to optimally function with clinically approved biomaterials or with endogenous ECM present at the delivery site. FIG. 2 shows that M-007 fulvate can improve the delivery, half-life, and effective communication of the growth factors selected by as much a 75 to 85%. In addition, the wound's natural healing mechanisms are accelerated as indicated by the curve profiles of FIG. 2. Although the mechanism involved in these improved sequences is not completely understood, there is no doubt that the fulvate molecule M-007 in all concentrations tested herein improve the healing cycle and reduce scaring.

Figure 3:
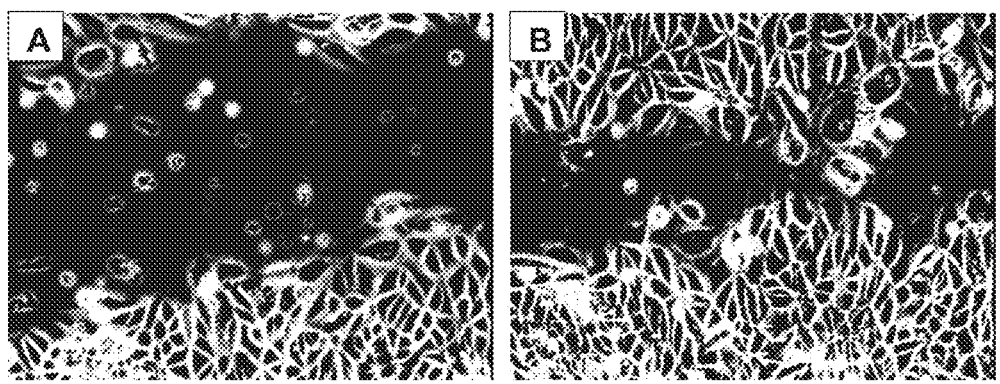
FIG. 3 shows the epidermal cell culture wounds in A) untreated group and B) treatment group with bFGF sol. No. 00376+M-007 fulvate sol. No. 00321A.

FIG. 3 shows the epidermal cell culture plates for A) non-treated control group compared to B) treated epidermal cell culture plate treated with bFGF sol. No. 00376+M-007 sol. No. 00321A.

Example 5

Combinations of M-007 and Interleukins

This example shows the therapeutic effects of combining M-007 with interleukins.

Major anti-inflammatory cytokines used in this research include interleukin (IL)-1 receptor antagonist, IL-6, IL-11, and IL-13. Specific cytokine receptors for IL-1, tumor necrosis factor-$\alpha$, and IL-18 also function as pro-inflammatory cytokine inhibitors.

The results of the screening tests showed that levels of cytokines increased only moderately in plasma on the test cell plates over a 24, and 48 hour period. Cytokine levels in the wound fluid were several folds higher. IL-6 in the wound fluid peaked at 7 hours after the cell plate preparation (271+/−135.8 pg/mL); IL-8 after 4 hours (11+/−9.4 ng/mL); sTNFR-1 at the second postoperative day (11.1+/−3.4 ng/mL). TGF-beta decreased at the first (15.2+/−8.6 ng/mL) and second (11.7+/−5.0 ng/mL) postoperative day. Based on these screening tests the cytokine IL-6 was chosen to be combined with M-007 fulvate.

Example 6

Effects of M-007 on Human $\beta$ Defensin

This example demonstrates that M-007 upregulates hBD.

The defensin hBD-1 is constitutively expressed in various epithelia. However, basal constitutive expression of hBD-1 in keratinocytes increases over time relative to the housekeeping gene $\beta$-actin (a 3-fold increase was found at 24 h and a 7-fold increase at 48 h for the IGF-1 stimulated keratinocytes as compared with the $\beta$-actin. However, expression was up-regulated ~50% compared with control at the mRNA level following 24- and 48-h stimulation with and between 85 and 90% for the M-007 treatment groups.

Another defensin, hBD-2, was found to be up-regulated in keratinocytes by IL-1 in keratinocytes. None of the other cytokines/growth factors induced the expression of hBD-2. mRNA for hBD-3 was not detected in unstimulated keratinocytes, but was significantly induced by TGF-$\alpha$. Although IGF-1 did not induce the expression of hBD-3, M-007 fulvate treatment resulted in an 8-fold higher mRNA levels. These results were found in response to a combination of M-007 titivate and TGF-α after 48 h of stimulation compared with stimulation with TGF-α, alone. This is consistent with the finding that IGF-1 and M-007 titivate causes trans-activation and trans-modulation of the EGF receptor, and thus potentially augments the effect of TGF-α, which binds to the EGF receptor. None of the pro-inflammatory cytokines or the other growth factors induced hBD-3. By immunoblot, hBD-3 was detected in the medium from keratinocytes stimulated with TGF-α, M-007 fulvate, and IGF-I/TGF-α, but not in the medium from unstimulated cells, thus demonstrating the induction of hBD-3 at the protein level. Immunostains of primary keratinocytes with antibodies against hBD-3 confirmed that hBD-3 peptide was induced to a greater extent by the M-007 fulvic molecule and to a lesser extent, by IGF-I/TGF-α than by TGF-α alone.

Example 7

Combinations of M-007 with Bioactive Fragmented Peptides

This example demonstrates the efficacy of combinations of M-007 with bioactive fragmented peptides for cell regeneration.

Two antimicrobial peptides (tigerinin-RC1: RVC-SAIPLPICH (SEQ ID NO: 9); tigerinin-RC2: RVC-MAIPLPLCH (SEQ ID NO: 10)) have been previously identified from the skin secretions of *Fejervarya cancrivora*. They have been found to exert wound-healing activity. Here, several peptides based on tigerinins are synthesized to screen candidates containing potential wound-healing ability. Among these peptides, a small peptide containing M-007 fulvate, was manifested to be a potent healer of skin wounds. M-007 fulvate isolated peptide (c [WCKPKPKPRCH-NH$_2$] (SEQ ID NO: 11)) was further synthesized and analyzed by HPLC and mass spectrometry to confirm purity. Molecular weight of the M-007 fulvate peptide was 1209.20 Da determined by MALDI-TOF mass spectral analysis, which indicated that the peptide was in cyclic form. The M-007 contained peptide was evaluated on skin cell plates at various concentrations in a standard saline solution, and later after dosage selection was combined into an M-007 fulvic serum.

Example 8

M-007 Effects on a Model Dermal Wound

This example demonstrates the efficacy of M-007 for wound healing.

Wound-healing represents a major health burden, such as diabetes-induced skin ulcers and burning. M-007 shows strong wound healing-promoting activity in a murine model of full thickness dermal wound. M-007 fulvate exerted significant effects on three stages of wound healing progresses including (1) the induction of macrophages recruitment to wound site at inflammatory reaction stage; (2) the promotion of the migration and proliferation both keratinocytes and fibroblasts, leading to re-epithelialization and granulation tissue formation; and (3) tissue remodeling phase, by promoting the release of transforming TGF-β1 and interleukin 6 (IL-6) in murine macrophages and activating mitogen-activated protein kinases (MAPK) signaling pathways. Considering its easy production, store and transfer and function to promote production of endogenous wound healing agents (TGF-β), M-007 fulvate acts as a biomaterial or template for the development of novel wound-healing agents.

Example 9

Animal Anti-Inflammatory Effects

This example demonstrates the safety and anti-inflammatory and wound-healing characteristics of M-007 in rats.

M-007 fulvate (≥100 mg/kg p.o.) effectively reduced carrageenan-induced paw edema in rats, which was comparable to 10 mg/kg p.o.), indomethacin. Topical application of M-007 fulvate formulated to contain 3.75% active product in a sterile petrolatum ointment at pH 4.98, compared favorably with commonly used fusidic acid cream (10 mg/g) in accelerating the healing of excised wounds infected with *Staphylococcus aureus*. No signs of toxicity were observed in rats during the 6-day acute and 3-month chronic treatment with M-007 titivate (100 mg/kg p.o.). Topical application of M-007 fulvate, formulated in UEA cream and applied to the right ears of mice at 400 mg/g body weight on days 1 and 7-38, produced no adverse events. No signs of toxicity were observed in the teratogenicity study, in which M-007 fulvate was administered at 100 mg/kg p.o. to pregnant female mice 3 days before fertilization to 14 days of pregnancy. In conclusion, M-007 fulvate is a safe compound with anti-inflammatory and wound-healing properties and merits further evaluation in the treatment of patients suffering from similar conditions.

Example 10

M-007 Promotes Cellular Proliferation

This example demonstrates that M-007 Fulvate promotes HaCat cell proliferation and migration.

Keratinocytes, fibroblasts or macrophages ($2\times10^4$ cells/mL) were separately cultured in wells of 96-well plate, and cells were incubated with various concentration M-007 fulvate (2.5, 5, 10, 20 μg/mL) or sterile H$_2$O alone for 24 h. After incubation with 5 mg/mL 3-(4,5-dimethylthiazol-2-yl)-2,5-diphenyltetrazolium bromide (MTT) for 4 h, absorbance was determined. Both HaCat keratinocytes and human skin fibroblasts (HSFs) were increased by when treated with M-007 fulvate, in a concentration dependent manner. Values are the mean±SE of three independent experiments. *$P<0.05$, **$P<0.01$ as compared between M-007 fulvate-stimulated and non-stimulated cells.

Example 11

Wound Healing Scratched Assay

This example demonstrates that M-007 is effective in treating wounds in an in vitro wound healing assay.

HaCat keratinocyte cells ($1\times10^6$) were seeded in a 6-well plate and cultured as monolayer to confluence overnight prior to serum starvation for 24 h. The monolayer was then scratched with a yellow 200 μl pipette tip to create an approximate 1-mm-wide wound area, and washed twice with PBS to remove floating cells. After the line scratch, 2 mL DMEM was added into every well to observe the effect of M-007 fulvate on keratinocytes migration. Cells were incubated with M-007 (20 μg/mL) for various time periods (from 0 h to 36 h), in the presence of mitomycin C (5 μg/mL) to prevent cell proliferation.

Wounded tissue initiates a complex and structured series of events in order to repair the damaged region. These events may include increased vascularization by angiogenic factors, an increase in cell proliferation and extracellular matrix deposition, and infiltration by inflammatory immune cells as part of the process to destroy necrotic tissue. The wound healing process begins as cells polarize toward the wound, initiate protrusion, migrate, and close the wound area. These processes reflect the behavior of individual cells as well as the entire tissue complex. Wound healing assays have been employed by researchers for years to study cell polarization, tissue matrix remodeling, or estimate cell proliferation and migration rates of different cells and culture conditions. Wound healing assays have been used to study cell polarity and actin cytoskeletal structure regulation through the role of Rho family GTPases, microtubule and Golgi apparatus orientation, the role of p53 in cell migration, as well as other physiological processes. These assays typically involve culturing a confluent cell monolayer and then displacing or destroying a group of cells by scratching a line through the monolayer. The open gap created by this "wound" is then inspected microscopically over time as the cells move in and fill the damaged area.

Figure 4:
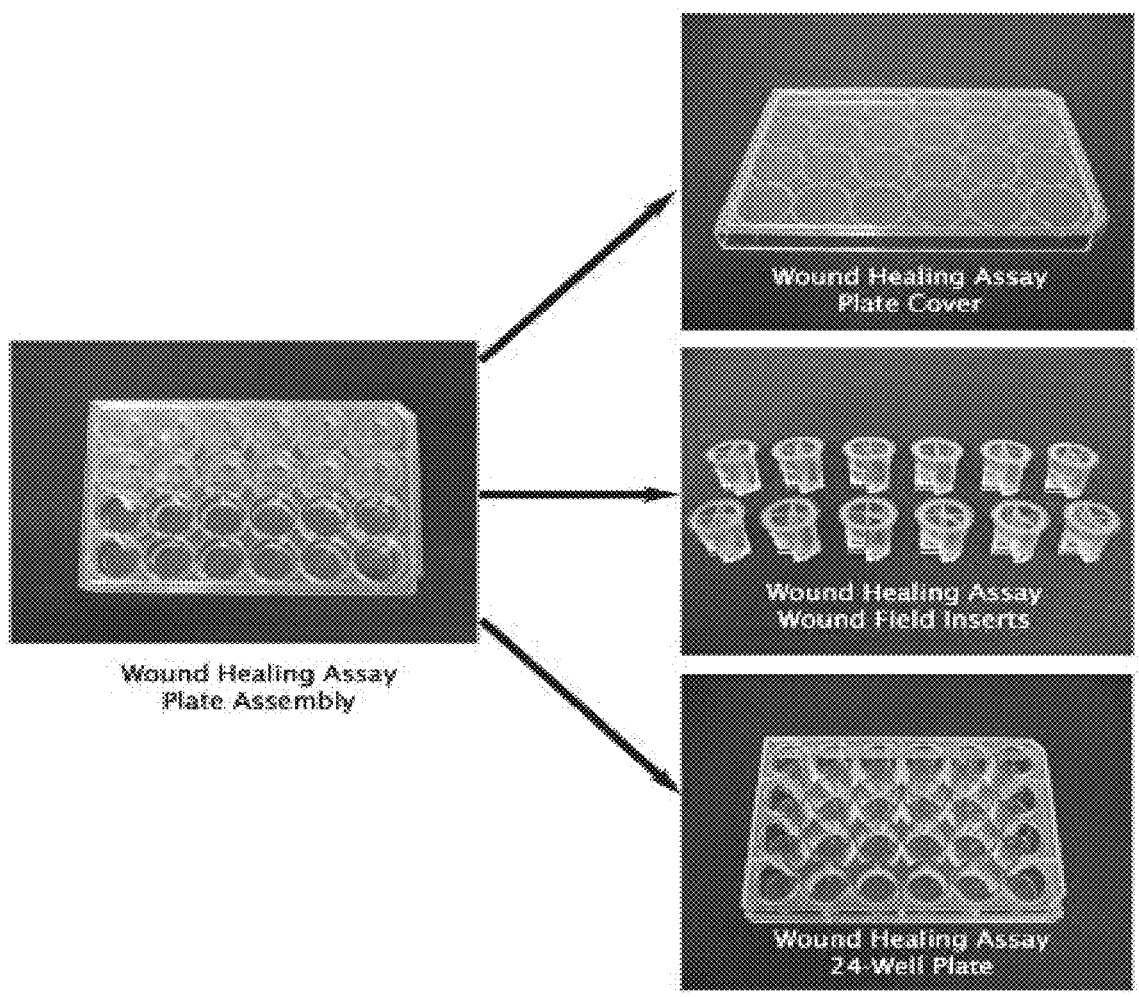
FIG. 4 is a depiction of the wound healing assay kit and setup used for the scratch assays to determine the efficacy of the compositions described herein in the healing process.
Figure 5:
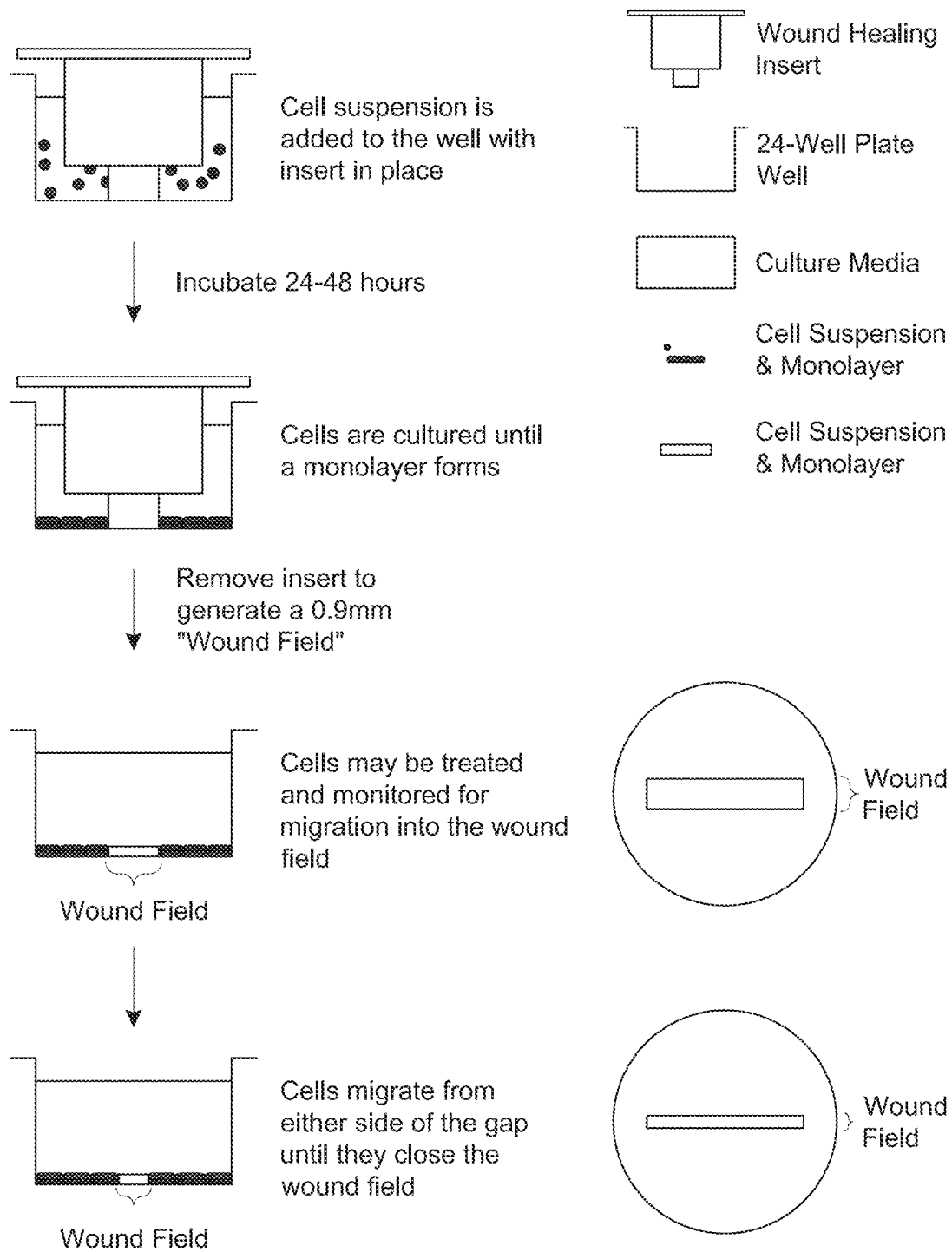
FIG. 5 shows a diagram of the experimental setup for the wound healing assay described herein.
Figure 7:
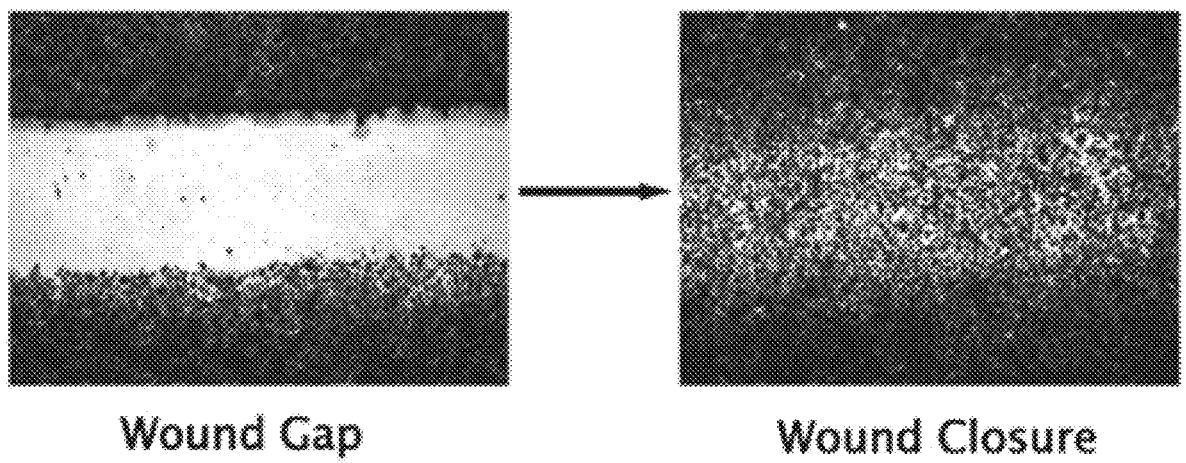
FIG. 7 shows the wound healing assay progression from 0% to 100% wound closure.

This "healing" effect can take several hours to several days depending on the cell type, conditions, and the surface area of the "wounded" region. The disadvantage of these "scratch wound" assays is the lack of a defined wound surface area, or gap between cells. Most of these wounds are varying sizes and widths, which inhibits consistent results and creates variation from well to well. In addition, the "scratch wound" assay often causes damage to the cells at the edge of the wound, which can prevent cell migration into the wound site and healing. This situation is overcome herein by developing an automatic starch stylus to generate a defined wound field or gap, after which an inert insert of specific thickness is inserted in the scratch/wound area. This method is depicted in FIG. 4 and FIG. 5. Cells are cultured until they form a monolayer around the insert. The insert is removed, leaving a precise 0.9 mm open "wound field" between the cells. Cells can be treated and monitored at this point for migration and proliferation into the wound field. Progression of these events can be measured by imaging samples fixed at specific time points or time-lapse microscopy. Migratory cells are able to extend protrusions and ultimately invade and close the wound field, as shown in FIG. 7. Cell proliferation and migration rates can be determined using manual fixing and microscopic imaging. A fixing solution is provided for stopping cells at specific time points as needed. Cell stain and DAPI stain are also used for viewing results with light and fluorescence microscopy.

A 24-well plate with CytoSelect™ Wound Healing Inserts is allowed to warm up at room temperature for 10 minutes. Using sterile forceps the desired number of inserts is oriented in the plate wells with the "wound field" aligned in the same direction. The inserts have firm contact with the bottom of the plate well. All samples are run in triplicate.

A cell suspension containing $0.5-1.0 \times 10^6$ cells/mL in media containing 10% fetal bovine serum (FBS). To this is added 500 µL of cell suspension to each well by carefully inserting the pipet tip through the open end at the top of the insert. For optimal cell dispersion, we add 250 µL of cell suspension to either side of the open ends at the top of the insert. Cells are incubated in a cell culture incubator overnight or until a monolayer forms. Insert are carefully removed from the well to begin the wound healing assay. Sterile forceps are used to grab and lift the insert from the plate well. Wells are slowly aspirate and the media discarded. Wells are washed with media to remove dead cells and debris. Media is then added to wells to keep cells hydrated. Wells are then visualized under a light microscope. If wells still have debris or unattached cells repeat wash. 9. When washing is complete, add media with FBS and/or compounds to continue cell culture and wound healing process. Agents that inhibit or stimulate cell migration can be added directly to the wells. Cells are placed in a cell culture incubator. For best results, a reticle micrometer measurement is used to create a defined surface area in order to monitor the closing, or "healing" of the wound. The center of the wound field is targeted and indicated in the scale sight. The defined surface area is created by multiplying the width of the wound field (0.9 mm) by the length, as shown in FIG. 6.

Figure 6:
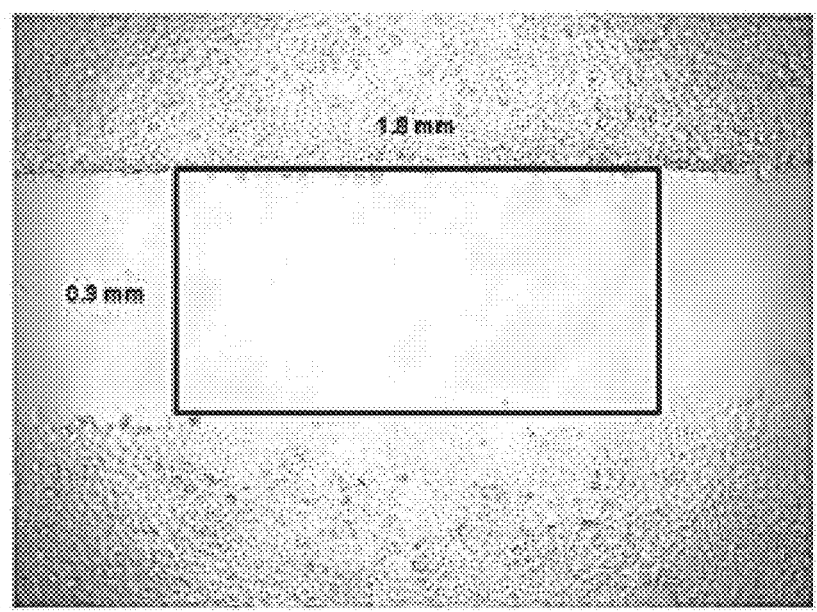
FIG. 6 shows an example of a wound field surface area. The wound closure is monitored with a light microscope or imaging software. The percent closure or the migration rate of the cells into the wound field is measured. Wound healing results were visualized with phase contrast, DAPI fluorescence labeling, or by cell staining.
Figure 8:
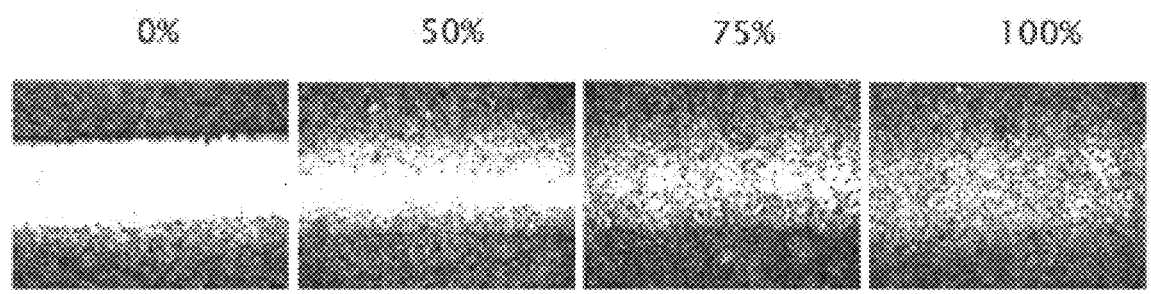
FIG. 8 depicts the percent closure of mouse embryonic fibroblasts/SIM mouse embryo fibroblasts (MEF/STO cells). As a control STO cells were tested using the CytoSelect™ 24—Well Wound Healing Assay. Cells were cultured 24 hours until a monolayer formed at which time the inserts were removed to begin the wound healing assay. Cells were monitored under phase contrast (not shown), DAPI labeling, and cell staining for determining percent closure (0, 50, 75, and 100%).

To calculate the results of the percent closure of the wound the surface area of the defined wound area is determined (see FIG. 6). The total surface area=0.9 mm×length. Next, the surface area of the migrated cells in to the wound area is determined. The migrated cell surface area=length of cell migration (mm)×2×length. Finally, the percent closure (%)=migrated cell surface area/total surface area×100. The migration rate is determined by determining the migration rate of cells into the defined wound area. Thus, the migration rate=length of cell migration (nm)/migration time (hr). FIG. 8 demonstrates typical results with the CytoSelect™ 24-well Wound Healing Assay Kit.

Images of the wounded cell monolayer were taken using a microscope (Olympus, Tokyo, Japan) at 0, 24, and 36 h after scratched wounding. Cell migration activity was expressed as the percentage of the gap relative to the total area of the cell-free region immediately after the scratch, named the repair rate of scarification, using Image J software (National Institutes of Health, Bethesda, Mich.), USA). The formula for repair rate of scarification %=(the gap width of 0 hour−temporal gap width)/the gap width of 0 hour×100%. For each plate, 6 randomly selected images were acquired. All experiments were independently carried out in triplicate. Values are the mean±SE of three independent experiments. Values are determined in percent of wound closure against time (days), as described previously.

During the healing of cutaneous wounds, keratinocytes migration is important. Pioneer keratinocytes, which early migrate to wound area and form a neo-epithelial tongue to cover the wound incision, consequently, in favor of proper and timely wound reparation. An in vitro cells scratch assay was performed to investigate the effect of M-007 fulvate on keratinocyte migration. Keratinocyte migration rate was based on the efficiency of monolayer cells invading the wound region with the M-007 fulvate treatment for 0 to 36 h. M-007 fulvate treatment significantly increased the migration rate of keratinocytes into the wound area. As expected, the pre-wound region appeared narrower than the vehicle control, which had a significantly larger denuded area following M-007 fulvate treatment for 24 h. Following treatment for 36 h, the M-007 fulvate-treated wound area was almost completely closed, whereas the control retained a wide gap. The repair rate of scarification was calculated by Image Comparison.

Example 12

M-007 Effects on Cytokine Secretion

This example demonstrates the effects of M-007 fulvate on cytokine excretion in murine cell line.

Many cytokines, such as TGF-β1, IL-6 and TNF-α have been a particular focus in recent research owing to their important roles in wound healing. The effects of M-007 fulvate on cytokines secretion in murine macrophages cell line RAW264.7 were tested using ELISA. TGF-β1 production was significantly increased in M-007 fulvate-stimulated supernatant compared with control. TGF-β1 concentration in supernatant was increased from 607.69 to 718.96 pg/mL (18.31%), 836.92 pg/mL (37.72%) and 951.92 pg/mL (56.65%) after the incubation of M-007 fulvate at 2.5, 5, 10, and 20 µg/mL for 16 h. IL-6 secretion was also increased in a concentration dependent manner in M-007 fulvate-treated cells. Compared with the baseline level of 51 pg/mL, 2.5, 5, 10, and 20 µg/mL M-007 fulvate induced 58, 60, 73 and 81 pg/mL IL-6 secretion, respectively. M-007 fulvate also affected IL-1β and TNF-α secretion at 3.6 and 4.1% by wt. vol. M-007 fulvate. M-007 fulvate promoted macrophages recruitment, TGF-β1 up-expression and myofibroblast differentiation.

Example 13

Ex Vivo Human Skin Treatment

This example demonstrates that M-007 induces wound closure in human skin explants.

The skin is the largest organ and its primary function is to serve as a protective barrier against outside environment and excessive water loss. Skin consists of two main tissue layers: a keratinized stratified epidermis and an underlying thick layer of collagen-rich dermal connective tissue providing support and nourishment. Impaired wound healing is a major complication underlying several disease processes (such as diabetes). Efficient wound healing is hampered by a wide variety of processes including hypoxia (oxygen deprivation), inflammation, infection, and oxidative stress through the generation of harmful reactive oxygen species (ROS). The inherent complexity of the healing wound has resulted in limited efficacy of most therapies that target single parameters involved in the slow healing processes. Fulvate fractions are organic bioactive polyelectrolyte acids from humic sources and have previously shown to exhibit a wide range of biological activities. Given that these molecules have been shown as potent anti-inflammatories and antioxidants we hypothesized that based on these properties fulvate fractions could aid in wound healing. We designed and synthesized a panel of fulvate derivatives and investigated their ability to accelerate wound healing using a modified scratch assay protocol, an ex vivo human skin model, and a mouse model of skin irritation. Several derivatives, and in particular M-007, supported cell migration, induced wound closure in human skin explants, and greatly accelerated the rate at which wound healing occurred in vivo. Therefore, fulvate derivatives are effective in wound healing therapies that may aid in wound healing treatment and are useful in cutaneous wound healing topical and injectable compositions.

The examples provided above show the therapeutic efficacy of M-007 fulvate alone or in combination with growth factors and/or with bioactive fragmented peptides. M-007 is an amino ion releasing hydrogen-bonded molecule. M-007 has been tested for verification by means of a series of sophisticated trials using nuclear magnetic resonance (NMR). All test results indicate this new molecule is essentially non-toxic with no side effects, and is considered as safe as distilled water. M-007 is a water-soluble blend of amino acids found naturally in fulvic compounds that embodies nature-based healing agents delivered through oral, inhalant, topical, and both inter- and intra-arterial or venous administration. M-007 facilitates healing across a broad spectrum of medical ailments and health conditions, through the free amino ions in hydrous solution inundate and bond to the nucleic acids within the unstable proteins of dysfunctional cells. The resultant biosynthesis causes the unstable proteins to align and become stable, returning the cells to their normal functioning as programmed by their original DNA coding which is still implanted within their DNA structure. This mechanism also causes reactivation of the proliferative phase regulated by the DNA, thus significantly accelerating the healing process. M-007 is derived from natural, based amino-acids in conjunction with the natural amino acids in the native fulvic acid fractions as well as peptides and enzymes that are enhanced by the fractionation of the fulvic acid molecule, selecting those amino and peptides that offer the most effective wound healing and cell growth beneficiation. The natural, non-toxic natures of the fulvic acid fraction M-007 ensure an FDA GRAS (Generally Recognized As Safe) status. The molecule is not a pharmaceutical drug. As described herein, it has multiple applications in the treatment of both human and animal health issues. The base M-007 fulvate is incorporated into a serial slurry, to which additional amino acids, nucleic acids, peptides and a wide verity of growth factors can be added making available a unique series of formula combinations. M-007 fulvate is a chemically pure pharmaceutical grade solution that is not only augmented with the amino fulvic molecule, but has the added benefits of a wide selection of (GF) to produce the most effective non-toxic, all-natural broad spectrum anti-fungal, anti-bacterial, anti-microbial, anti-viral agent wound healing source currently available. This new formulation gives it the propensity to more easily bond to the nucleic acids within the cellular protein and causes the nucleus to function as originally programmed by its DNA. The addition of fulvic acid to M-007 aids in the bonding process because fulvate strongly bond to all proteins. Toxic microbes, viruses and fungi do not and cannot form immunity to the action of the fulvate component of the M-007 moiety due to its superb ability to bond to the protein portion of the covering membrane of microbial cells, viral forms and fungi. M-007 fulvate is a non-specific entry inhibitor to viral coat proteins. It exhibits broad spectrum anti-viral activity against most envelope viruses such as Vaccinia, Herpes, HIV Hepatitis C, and Influenza, including H5N1.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member, Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating skin or hair damage with a composition prepared by providing an aqueous slurry comprising humified organic matter, applying the aqueous slurry to high pressure column fractionation to obtain fractionated samples, applying the fractionated samples to molecular sieving, and isolating a fulvate fraction, the method comprising:
  administering to a subject in need thereof the composition, wherein the composition comprises a therapeutically effective amount of an isolated fulvate fraction having a molecular formula of $C_{12}H_{16}O_9$ and having an average molecular weight ranging from 80 to 350 Da, as measured by vapor pressure osmometry.

2. The method of claim 1, wherein the topical composition further comprises a growth factor or a bioactive peptide.

3. The method of claim 1, wherein the isolated fulvate fraction has an average molecular weight ranging from 300 to 320 Da.

4. The method of claim 1, wherein the isolated fulvate fraction has an average molecular weight of about 308.24 Da.

5. The method of claim 1, wherein the isolated fulvate fraction has an average molecular weight of about 309 Da.

6. The method of claim 1, wherein the isolated fulvate fraction is present in the topical composition in an amount ranging from about 0.5% to about 65% by weight.

7. The method of claim 2, wherein the growth factor is EGF, PDGF, FGF, TGF-α, TGF-β, NGF, EPO, IGF-I, IGF-II, IL-1α, IL-1β, IL-2, IL-3, IL-4, IL-5, IL-6, IL-7, IL-8, IL-9, IL-10, IL-11, IL-12, IL-13, IFN-α, IFN-β, IFN-γ, TNFα, TNF-β, GM-CSF, M-CSF, VEGF, HGF, KGF, or combinations thereof.

8. The method of claim 2, wherein the bioactive peptide is a tigerinin-based peptide.

9. The method of claim 2, wherein the bioactive peptide is Syndermin palmitoyl tripeptide-1 amide, Synepin palmitoyl sh-tripeptide-3 amide, Binterin palmitoyl sh-tripeptide-4 amide, Winhibin palmitoyl sh-tripeptide-53 amide, Adiponin palmitoyl sh-tripeptide-1 amide, or combinations thereof.

10. The method of claim 1, wherein the topical composition is formulated as a liquid, lotion, cream, gel, cosmetic, or serum.

11. The method of claim 1, wherein applying the topical composition induces recruitment of macrophages, promotes migration and proliferation of keratinocytes and fibroblasts, and promotes cytokine secretion.

* * * * *